(12) United States Patent
Cunningham et al.

(10) Patent No.: US 6,372,719 B1
(45) Date of Patent: Apr. 16, 2002

(54) $\alpha_v\beta_3$ INTEGRIN ANTAGONISTS IN COMBINATION WITH CHEMOTHERAPEUTIC AGENTS

(76) Inventors: Jay Cunningham, 3733 N. Bell Ave., Chicago, IL (US) 60618; Gary B. Gordon, 3282 University Ave., Highland Park, IL (US) 60035; G. Allen Nickols, 2690 Lenee La., Wentzville, MO (US) 63385; William F. Westlin, 15989 Woodlet Park Ct., Chesterfield, MO (US) 63017; Thomas Edward Rogers, 755 Trago Creek Dr., Ballwin, MO (US) 63021; Peter Gerrard Ruminski, 7687 Pierside Dr., Dardenne Prairie, MO (US) 63366

( * ) Notice: Subject to any disclaimer, the term of this patent is extended or adjusted under 35 U.S.C. 154(b) by 0 days.

(21) Appl. No.: 09/262,725

(22) Filed: Mar. 4, 1999

Related U.S. Application Data

(63) Continuation-in-part of application No. 09/034,270, filed on Mar. 4, 1998, now abandoned.

(51) Int. Cl.[7] ............... A61K 31/70; A61K 31/66; A61K 31/505; A61K 31/335; A61K 31/24
(52) U.S. Cl. ............... 514/34; 574/110; 574/272; 574/274; 574/449; 424/649
(58) Field of Search ............... 514/272, 274, 514/449, 34, 110; 424/649

(56) References Cited

U.S. PATENT DOCUMENTS 6,013,651 A * 1/2000 Rogers et al. ............... 514/269

FOREIGN PATENT DOCUMENTS

| WO | WO 97 08145 | 3/1997 |
| WO | WO 98/14192 | 4/1998 |
| WO | WO 98/31359 | 7/1998 |

OTHER PUBLICATIONS

Carter et al., Chemotherpy of Cancer, sec. ed., John Wiley & Sons, N.Y., N.Y., pp. 107–108, Aug. 13, 1981.*
Pommier, Y. et al., "HIV–1 Integrase as target for antiviral drugs," Antiviral Chemistry & Chemotherapy, vol. 8 (No. 6), pp. 463–483, 1997.
Nicklaus, M.C. et al., "HIV–1 Integrase Pharmacophore: Discovery of Inhibitors through Three–Dimensional Database Searching," J. Med. Chem, 7th ed., American Chemical Society, v. 40, pp. 920–929, 1997.
Hong, H. et al., "Discovery of HIV–1 Integrase Inhibitors by Pharmacophore Searching" J. Med. Chem, American Chemical Society, v. 40, pp. 930–936, 1997.
Fields, Gregg B., "Integrins: cell adhesion molecules in cancer," Exp. Opin. Ther. Patents, Ashley Publications Ltd., vol. 8 (No. 6), pp. 633–644, 1998.

* cited by examiner

*Primary Examiner*—Jerome D. Goldberg
(74) *Attorney, Agent, or Firm*—Alan Scrivner; Rachel Polster

(57) ABSTRACT

The present invention is directed to compounds of the formula

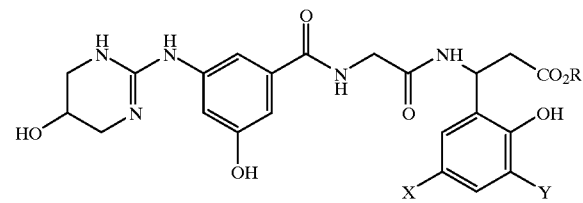

and pharmaceutically acceptable salts and isomers thereof administered in combination with chemotherapeutic agents.

13 Claims, No Drawings

$\alpha_v\beta_3$ INTEGRIN ANTAGONISTS IN COMBINATION WITH CHEMOTHERAPEUTIC AGENTS The present application is a C-I-P of U.S. Ser. No. 09/034,270 filed Mar. 4, 1998, now abandoned.

FIELD OF THE INVENTION

The present invention relates to the use of pharmaceutical agents (compounds) which are known as $\alpha$hd v$\beta_3$ integrin antagonists in combination with chemotherapeutic agents and methods for using the same for treatment or prevention of neoplasia diseases.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked $\alpha$ and $\beta$ polypeptide subunits. Currently eleven different $\alpha$ subunits have been identified and six different $\beta$ subunits have been identified. The various a subunits can combine with various $\beta$ subunits to form distinct integrins.

The integrin identified as $\alpha_v\beta_3$ (also known as the vitronectin receptor) has been identified as an integrin associated with endothelial cells and smooth muscle cells. $\alpha_v\beta_3$ integrins can promote the formation of blood vessels (angiogensis) in tumors. These vessels nourish the tumors and provide access routes into the bloodstream for metastatic cells.

The $\alpha_v\beta_3$ integrin is known to play a role in various conditions or disease states including tumor metastasis, solid tumor growth (neoplasia), osteoporosis, Paget's disease, humoral hypercalcemia of malignancy, angiogenesis, including tumor angiogenesis, retinopathy, including macular degeneration, arthritis, including rheumatoid arthritis, periodontal disease, psoriasis and smooth muscle cell migration (e.g. restenosis). Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. Therefore, $\alpha_v\beta_3$ antagonists would be useful therapeutic targets for treating such conditions associated with neovascularization (Brooks et al., Science, Vol. 264, (1994), 569–571).

A neoplasm or tumor, is an abnormal, unregulated, and disorganized proliferation of cell growth. A neoplasm is malignant, or cancerous, if it has properties of destructive growth, invasiveness and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphotics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

Cancer is now the second leading cause of death in the United States. However, cancer is not fully understood at the molecular level. It is known that exposure of a cell to a carcinogen leads to DNA alteration that inactivates a suppressive gene or activates an oncogene.

Suppressive genes are growth regulatory genes, which upon mutation, can no longer control cell growth. Oncogenes are initially normal genes (called prooncogenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

Cancer is now primarily treated with one or a combination of three types of therapies: surgery, radiation and chemotherapy. Surgery involves the bulk removal of diseased tissue. While surgery is sometimes effective in removing tumors located at certain sites, for example, in the breast, colon and skin, it cannot be used in the treatment of tumors located in other areas, such as the backbone, nor in the treatment of disseminated neoplastic conditions such as leukemia.

Chemotherapy involves the disruption of all replication or cell metabolism. It is used most often in the treatment of breast, lung and testicular cancer. Many adverse effects are experienced by patients undergoing systemic chemotherapy for treatment of neoplastic diseases. Chemotherapy-induced side effects significantly impact the quality of life of the patient and may dramatically influence patient compliance with treatment.

SUMMARY OF THE INVENTION

The present invention relates to the use of compounds of the following general formula

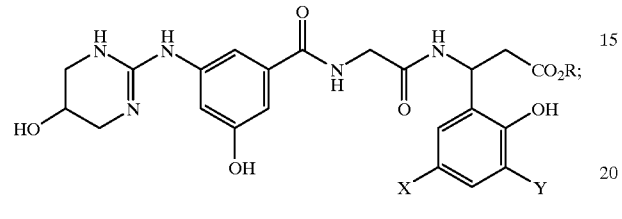

wherein X and Y are the same or different halo group; R is H or alkyl; and pharmaceutically acceptable salts thereof in combination with chemotherapeutic agents and methods for using the combinations for treatment or prevention of neoplasia diseases.

The compounds described above can exist in various isomeric forms and all such isomeric forms are meant to be included. Tautomeric forms are also included as well as pharmaceutically acceptable salts of such isomers and tautomers.

DETAILED DESCRIPTION

The present invention relates to a class of compounds known as $\alpha_v\beta_3$ integrin antagonists represented by the following formulae I–XVIII, in combination with chemotherapeutic agents, more fully described below, and methods of using such combinations for treatment or prevention of neoplasia diseases.

(I)

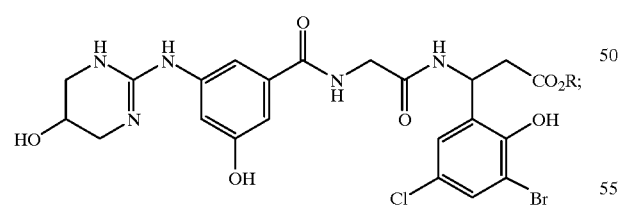

(II)

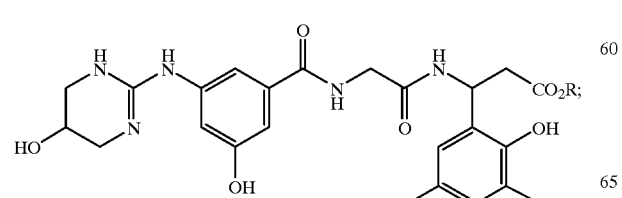

(III)

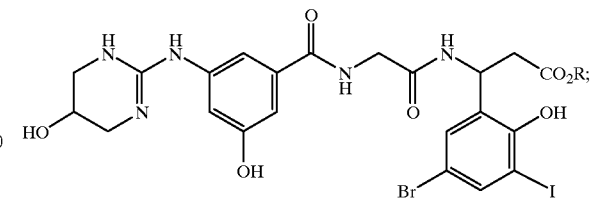

(IV)

(V)

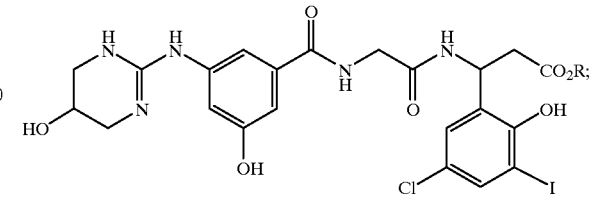

(VI)

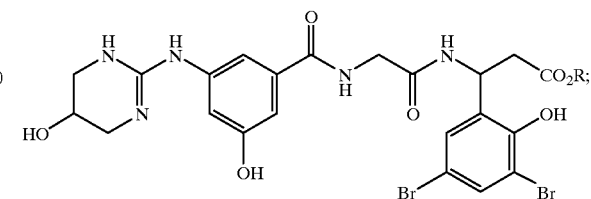

(VII)

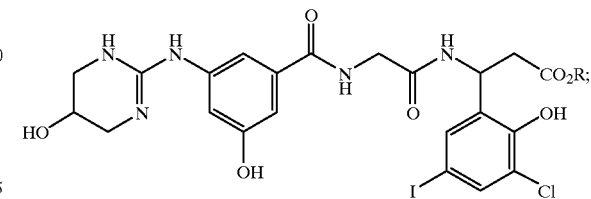

(VIII)

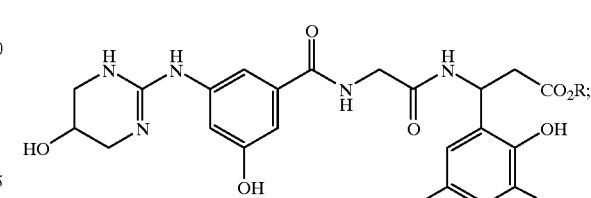

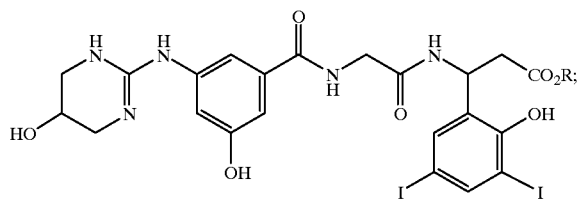

(IX)

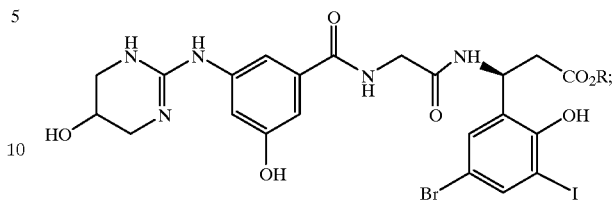

(XV)

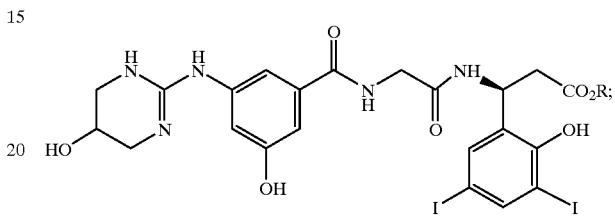

(X)

(XVI)

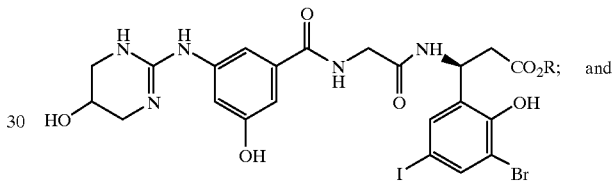

(XI)

(XVII)

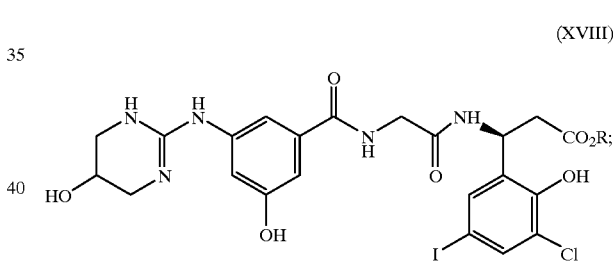

(XII)

(XVIII)

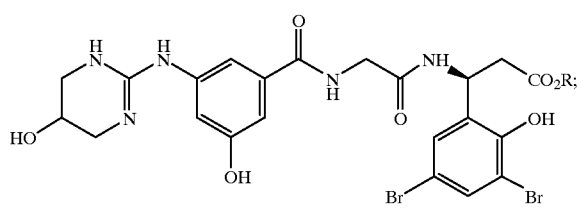

(XIII)

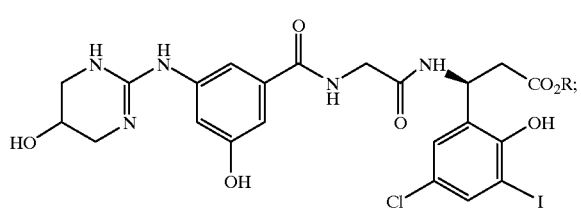

(XIV)

wherein R is H or lower alkyl and pharmaceutically acceptable salts thereof.

Among chemotherapuetic agents that may be used in combination with the $\alpha_v\beta_3$ antagonist compounds include, but are not limited to, 5-fluorouacil, cyclophosphamide, cisplatin, taxol and doxorubicin are preferred. Other chemotherapeutics useful in combination and within the scope of the present invention include, but are not limited to, buserelin, topoisomerase inhibitors such as topotecan and irinotecan, mitoxantrone, BCNU, CPT-11, chlorotranisene, chromic phosphate, gemcitabine, dexamethasone, estradiol, estradiol valerate, estrogens conjugated and esterified, estrone, ethinyl estradiol, floxuridine, goserelin, hydroxyurea, carboplatin, melphalan, methotrexate, mitomycin and prednisone. Table I lists other chemotherapeutic agents which can be used in the present invention.

Table I provides known median dosages for selected chemotherapeutic agents which may be useful in combination with the $\alpha_v\beta_3$ antagonist compounds and compositions.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the term "halo" or "halogen" refers to bromo, chloro, or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

| | |
|---|---|
| $^1$H-NMR = | proton nuclear magnetic resonance |
| AcOH = | acetic acid |
| Ar = | argon |
| $CH_3CN$ = | acetonitrile |
| CHN analysis = | carbon/hydrogen/nitrogen elemental analysis |
| CHNCl analysis = | carbon/hydrogen/nitrogen/chlorine elemental analysis |
| CHNS analysis = | carbon/hydrogen/nitrogen/sulfur elemental analysis |
| DI water = | deionized water |
| DMA = | N,N-dimethylacetamide |
| DMAP = | 4-(N,N-dimethylamino)pyridine |
| DMF = | N,N-dimethylformamide |
| EDCl = | 1-(3-dimethylaminopropyl)-3-ethylcarbodiimide hydrochloride |
| EtOAc = | ethyl acetate |
| EtOH = | ethanol |
| FAB MS = | fast atom bombardment mass spectroscopy |
| g = | gram(s) |
| HOBT = | 1-hydroxybenzotriazole hydrate |
| HPLC = | high performance liquid chromatography |
| IBCF = | isobutylchloroformate |
| KSCN = | potassium thiocyanate |
| L = | liter |
| LiOH = | lithium hydroxide |
| MEM = | methoxyethoxymethyl |
| MEMCl = | methoxyethoxymethyl chloride |
| MeOH = | methanol |
| mg = | milligram |
| $MgSO_4$ = | magnesium sulfate |
| ml = | milliliter |
| mL = | milliliter |
| MS = | mass spectroscopy |
| MTBE = | methyl tert-butyl ether |
| $N_2$ = | nitrogen |
| $NaHCO_3$ = | sodium bicarbonate |
| NaOH = | sodium hydroxide |
| $Na_2SO_4$ = | sodium sulfate |
| NMM = | N-methylmorpholine |
| NMP = | N-methyl pyrrolidinone |
| NMR = | nuclear magnetic resonance |
| $P_2O_5$ = | phosphorous pentoxide |
| PTSA = | para-toluenesulfonic acid |
| RPHPLC = | reverse phase high performance liquid chromatography |
| RT = | room temperature |
| TFA = | trifluoroacetic acid |
| THF = | tetrahydrofuran |
| TMS = | trimethylsilyl |
| Δ = | heating the reaction mixture |

The compounds described herein can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound described above with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, tartrate salts and the like. All of the pharmacologically acceptable salts may be prepared by conventional means. (See Berge et al., *J Pharm. Sci.,* 66(1), 1–19 (1977) for additional examples of pharmaceutically acceptable salts.)

Treatment or prevention of a neoplasia disease in a mammal is provided by methods and combinations using one or more $\alpha_v\beta_3$ integrin antagonist described above with one or more chemotherapeutic agents described above. The method comprises treating a mammal with a therapeutically effective amount of an $\alpha_v\beta_3$ integrin antagonist in combination with a chemotherapeutic agent.

$\alpha_v\beta_3$ inhibitors are being developed as potential anticancer agents. Compounds that impair endothelial cell adhesion via the $\alpha_v\beta_3$ integrin induce improperly proliferating endothelial cells to die.

The $\alpha_v\beta_3$ integrin has been shown to play a role in melanoma cell invasion (Seftor et al., Proc. Natl. Acad. Sci. USA, 89: 1557–1561, 1992). The $\alpha_v\beta_3$ integrin expressed on human melanoma cells has also been shown to promote a survival signal, protecting the cells from apoptosis (Montgomery et al., Proc. Natl. Acad. Sci., USA, 91: 8856–8860, 1994).

Mediation of the tumor cell metastatic pathway by interference with the $\alpha_v\beta_3$ integrin cell adhesion receptor to impede tumor metastasis would be beneficial. Antagonists of $\alpha_v\beta_3$ have been shown to provide a therapeutic approach for the treatment of neoplasia (inhibition of solid tumor growth) because systemic administration of $\alpha_v\beta_3$ antagonists causes dramatic regression of various histologically distinct human tumors (Brooks et al., Cell, 79: 1157–11164, 1994).

The adhesion receptor identified as integrin $\alpha_v\beta_3$ is a marker of angiogenic blood vessels in chick and man. This receptor plays a critical role in angiogenesis or neovascularization. Angiogenesis is characterized by the invasion, migration and proliferation of smooth muscle and endothelial cells by new blood vessels. Antagonists of $\alpha_v\beta_3$ inhibit this process by selectively promoting apoptosis of cells in the neovasculature. The growth of new blood vessels also contributes to pathological conditions such as diabetic retinopathy (Adamis et al., Amer. J. Opthal., 118: 445–450, 1994) and rheumatoid arthritis (Peacock et al., J. Exp. Med., 175:, 1135–1138, 1992). Therefore, $\alpha_v\beta_3$ antagonists can be useful therapeutic targets for treating such conditions associated with neovascularization (Brooks et al., Science, 164: 569–571, 1994).

There are five major classes of chemotherapeutic agents currently in use for the treatment of cancer: natural products and their derivatives; anthracyclins; alkylating agents; antimetabolites; and hormonal agents. Chemotherapeutic agents are often referred to as antineoplastic agents.

The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastrointestinal mucosa and fetal tissue.

Antimetabolites are typically reversible or irreversible enzyme inhibitors, or compounds that otherwise interfere with the replication, translation or transcription of nucleic acids.

Several synthetic nucleosides have been identified that exhibit anticancer activity. A well known nucleoside derivative with strong anticancer activity is 5-fluorouacil. 5-Fluorouracil has been used clinically in the treatment of malignant tumors, including, for example, carcinomas, sarcomas, skin cancer, cancer of the digestive organs, and breast cancer. 5-Fluorouacil, however, causes serious adverse reactions such as nausea, alopecia, diarrhea, stomatitis, leukocytic thrombocytopenia, anorexia, pigmentation and edema.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma.

The following table provides illustrative examples of median dosages for selected cancer agents that may be used in combination with an $\alpha_v\beta_3$ integrin antagonist agent. It should be noted that the specific dose regimen for the chemotherapeutic agents below will depend upon dosing considerations based upon a variety of factors including the type of neoplasia; the state of the neoplasm; the age, weight, sex, and medical condition of the patient; the route of administration; the renal and hepatic function of the patient; and the particular combination employed.

TABLE I

| NAME OF CHEMOTHERAPEUTIC AGENT | MEDIAN DOSAGE |
| --- | --- |
| Asparaginase | 10,000 units |
| Bleomycin Sulfate | 15 units |
| Carboplatin | 50–450 mg. |
| Carmustine | 100 mg. |
| Cisplatin | 10–50 mg. |
| Cladribine | 10 mg. |
| Cyclophosphamide (lyophilized) | 100 mg.–2 gm. |
| Cyclophosphamide (non-lyophilized) | 100 mg.–2 gm. |
| Cytarabine (lyophilized powder) | 100 mg.–2 gm. |
| Dacarbazine | 100 mg.–200 mg. |
| Dactinomycin | 0.5 mg |
| Daunorubicin | 20 mg. |
| Diethylstilbestrol | 250 mg. |
| Doxorubicin | 10–150 mg. |
| Etidronate | 300 mg. |
| Etoposide | 100 mg. |
| Floxuridine | 500 mg. |
| Fludarabine Phosphate | 50 mg. |

TABLE I-continued

| NAME OF CHEMOTHERAPEUTIC AGENT | MEDIAN DOSAGE |
| --- | --- |
| Fluorouracil | 500 mg.–5 gm. |
| Goserelin | 3.6 mg. |
| Granisetron Hydrochloride | 1 mg. |
| Idarubicin | 5–10 mg. |
| Ifosfamide | 1–3 gm. |
| Leucovorin Calcium | 50–350 mg. |
| Leuprolide | 3.75–7.5 mg. |
| Mechlorethamine | 10 mg. |
| Medroxyprogesterone | 1 gm. |
| Melphalan | 50 gm. |
| Methotrexate | 20 mg.–1 gm. |
| Mitomycin | 5–40 mg. |
| Mitoxantrone | 20–30 mg. |
| Ondansetron Hydrochloride | 40 mg. |
| Paclitaxel | 30 mg. |
| Pamidronate Disodium | 30–90 mg. |
| Pegaspargase | 750 units |
| Plicamycin | 2,500 mcgm. |
| Streptozocin | 1 gm. |
| Thiotepa | 15 mg. |
| Teniposide | 50 mg. |
| Vinblastine | 10 mg. |
| Vincristine | 1–5 mg. |

The compounds of the formula I–XVIII are potent and selective, orally available, small molecule peptidomimetic antagonists of $\alpha_v\beta_3$. These compounds were designed to explore the utility of $\alpha_v\beta_3$ antagonists in preclinical models of angiogensis and solid tumor growth. XII was found to be a potent ($IC_{50}<1$ nM) and selective ($IC_{50}=0.2_\mu$M vs $\alpha_{IIb}\beta_3$) antagonist of $\alpha_v\beta_3$ in vitro. Human microvessel endothelial cell proliferation and migration was found to be dependent on $\alpha_v\beta_3$ and XII dose-dependently inhibited these functions. In vivo, XII was a potent inhibitor of angiogenesis. Oral administration of XII (40 mg/kg) significantly inhibited angiogenesis in the mouse corneal micropocket assay. Moreover, XII was a potent inhibitor of solid tumor growth in vivo. XII dose-dependently inhibited M21 human melanoma tumor growth in SCID mice over a dose range of 0.2–30 mg/kg. Inhibition of tumor growth with XII was additive to that using the chemotherapeutic agent, cisplatin, at a maximum tolerated dose. Together, these results suggest that the $\alpha_v\beta_3$ antagonists described herein will be effective therapeutic agents against the growth of solid tumors in the clinic.

Implantation of Rice Leydig tumor cells subcutaneously in the flank of SCID mice led to the growth of a large tumor (volume>1500 mm$^3$) within 11 days and the development of severe hypercalcemia (>15 mg/dl). The $\alpha_v\beta_3$ antagonist XII administered orally, inhibited tumor growth and hypercalcemia in a dose-dependent manner. Cisplatin treatment (maximum tolerated dose) of tumor bearing mice inhibited tumor growth by approximately 50%. XII (10 mg/kg, PO) alone inhibited growth by 10%, but in combined therapy with cisplatin, tumor growth was reduced 80% compared to control-treated mice. Survival in this model is a function of hypercalcemia as well as tumor growth. Cisplatin or XII alone had little effect on survival time. However, the combined cisplatin and XII treatment almost doubled overall survival. These results clearly demonstrate the efficacy of the orally administered $\alpha_v\beta_3$ antagonist, XII, to reduce the growth of a solid tumor and associated hypercalcemia when used as monotherapy. Moreover, XII in combination with the chemotherapeutic agent, cisplatin, was shown to have superior efficacy to either agent alone. XII and other similar $\alpha_v\beta_3$ antagonists should provide important therapeutic opportunities to treat cancer.

The methods and combination therapy of the present invention provide one or more benefits. Combinations of $\alpha_v\beta_3$ integrin antagonists with chemotherapeutic agents are useful in treating and preventing neoplasia diseases. Preferably, the $\alpha_v\beta_3$ integrin antagonist agent or agents and the chemotherapeutic compounds, compositions, agents and therapies of the present invention are administered in combination at a low dose, that is, at a dose lower than has been conventionally used in clinical situations for each of the individual components administered alone.

A benefit of lowering the dose of the compounds, compositions, agents and therapies of the present invention administered to a mammal includes a decrease in the incidence of adverse effects associated with higher dosages. For example, by lowering the dosage of a chemotherapeutic agent such as methotrexate, a reduction in the frequency and the severity of nausea and vomiting will result when compared to that observed at higher dosages. Similar benefits are contemplated for the compounds, compositions, agents and therapies in combination with the $\alpha_v\beta_3$ integrin antagonist agents of the present invention.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

When administered as a combination, the therapeutic agents can be formulated as separate compositions which are given at the same time or different times, or the therapeutic agents can be given as a single composition.

When used as a therapeutic agent the compounds described herein are preferably administered with a physiologically acceptable carrier. A physiologically acceptable carrier is a formulation to which the compound can be added to dissolve it or otherwise facilitate its administration. Examples of physiologically acceptable carriers include, but are not limited to water, saline, physiologically buffered saline. Additional examples are provided below.

The $\alpha_v\beta_3$ integrin antagonist compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The $\alpha_v\beta_3$ integrin antagonist compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar in the medicinal arts.

The present invention provides a method of treating or preventing neoplasia diseases which method comprises administering a therapeutically effective amount of a compound selected from the class of $\alpha_v\beta_3$ integrin antagonist compounds described above, in combination with a chemotherapeutic agent, wherein one or more compound is administered in association with one or more non-toxic, pharmaceutically acceptable carrier and/or diluent and/or adjuvant (collectively referred to herein as "carrier" materials) and if desired other active ingredients.

Based upon standard laboratory experimental techniques and procedures well known and appreciated by those skilled in the art, as well as comparisons with compounds of known usefulness, the compounds described above can be used in the treatment of patients suffering from neoplasia diseases. One skilled in the art will recognize that selection of the most appropriate $\alpha_v\beta_3$ integrin antagonist+ chemotherapeutic compound of the invention is within the ability of one with ordinary skill in the art and will depend on a variety of factors including assessment of results obtained in standard assay and animal models.

Treatment of a patient afflicted with neoplasia disease comprises administering to such a patient an amount of $\alpha_v\beta_3$ integrin antagonist compound in combination with a chemotherapeutic agent described above which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

The dosage regimen for the compounds and/or compositions containing the compounds is based on a variety of factors, including the type, age, weight, sex and medical condition of the patient; the severity of the condition; the type of neoplasia disease; the route of administration; and the activity of the particular compound employed. Thus the dosage regimen may vary widely. Dosage levels of the order from about 0.01 mg to about 1000 mg per kilogram of body weight per day of the $\alpha_v\beta_3$ integrin antagonist compounds are useful in the treatment of the neoplasia diseases, and more preferably from about 0.01 mg to about 100 mg per kg of body weight per day. The amount that can be combined with the chemotherapeutic agent to produce a single dosage form will vary depending upon the host treated and the particular mode of administration.

The active $\alpha_v\beta_3$ integrin antagonist ingredient administered by injection is formulated as a composition wherein, for example, saline, dextrose or water may be used as a suitable carrier. A suitable daily dose would typically be about 0.01 to 10 mg/kg body weight injected per day in multiple doses depending on the factors listed above.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, andlor polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

It is understood that a specific dose level for any particular patient will depend upon a variety of factors including the activity of the specific compound employed, the age, body weight, general health, sex, diet, time of administration, rate of excretion, drug combination, and the severity of the particular neoplasia disease being treated and form of administration.

Treatment dosages generally may be titrated to optimize safety and efficacy. Typically, dosage-effect relationships from an initial in vitro analysis can provide useful guidance on the proper doses for patient administration. Studies in animal models also generally may be used for guidance regarding effective dosages for treatment of cancers in accordance with the present invention. In terms of treatment protocols, it should be appreciated that the dosage to be administered will depend on several factors, including the particular agent that is administered, the route administered, the condition of the particular patient, etc. It will generally be desirable to administer the $\alpha_v\beta_3$ integrin antagonist agents either orally, parenterally, intravenously, or subcutaneously. Other routes of administraton are also contemplated, including intranasal and transdermal routes, and by inhalation. Generally speaking, one will desire to administer an amount of the agent that is effective to achieve a serum level commensurate with the concentrations found to be effective in vitro. Thus, where an agent is found to demonstrate in vitro activity at, e.g., 10 $\mu$M, one will desire to administer an amount of the drug that is effective to provide about a 10 $\mu$M concentration in vivo. Determination of these parameters are well within the skill of the art. These considerations, as well as effective formulations and administration procedures are well known in the art and are described in standard textbooks.

Any effective treatment regiment can be utilized and readily determined and repeated as necessary to effect treatment. In clinical practice, the compositions containing the $\alpha_v\beta_3$ integrin antagonist alone or in combination with other therapeutic agents can be administered in specific cycles until a response is obtained.

For patients who are without advanced or metastatic cancer, an $\alpha_v\beta_3$ integrin antagonist based drug in combination with one or more anticancer agents can be administered as an immediate initial therapy prior to surgery, chemotherapy, or radiation therapy, and as a continuous post-treatment therapy in patients at risk for recurrence or metastasis. The goal in these patients is to inhibit the growth of potentially metastatic cells from the primary tumor during surgery or radiotherapy and inhibit the growth of tumor cells from undetectable residual primary tumor.

For patients who are with advanced or metastatic cancer, an $\alpha_v\beta_3$ integrin antagonist based drug in combination with one or more anticancer agents of the present invention can be used as a continuous supplement to, or possible replacement for, hormonal ablation. The goal in these patients is to slow or prevent tumor cell growth from both the untreated primary tumor and from the existing metastatic lesions.

In addition, the invention may be particularly efficacious during post-surgical recovery, where the present compositions and methods may be particularly effective in lessening the chances of recurrence of a tumor engendered by shed cells that cannot be removed by surgical intervention.

The $\alpha_v\beta_3$ integrin antagonist may be used in conjunction with one or more other treatment modalities, including, but not limited to surgery and radiation, hormonal therapy, immunotherapy, and cryotherapy. The present invention can be used in conjunction with any current or future therapy.

The phrase "combination therapy" (or "co-therapy"), in defining the use of an $\alpha_v\beta_3$ integrin antagonist compound and chemotherapeutic agent or therapy of the present invention, is intended to embrace administration of each agent or therapy in a sequential manner in a regimen that will provide beneficial effects of the combination, and is intended as well to embrace co-administration of these agents or therapies in a substantially simultaneous manner, such as in a single capsule having a fixed ratio of these active agents or in multiple, separate capsules for each agent.

The term "treatment" refers to any process, action, application, therapy, or the like, wherein a mammal, including a human being, is subject to medical aid with the objective of improving the mammal's condition, directly or indirectly.

The term "inhibition", in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors amongst others. In the extreme, complete inhibition, is referred to herein as prevention.

The term "prevention," in relation to neoplasia, tumor growth or tumor cell growth, means no tumor or tumor cell growth if none has occurred, and no further tumor or tumor cell growth if there had already been tumor growth.

The term "angiogenesis" refers to the process by which tumor cells trigger abnormal blood vessel growth to create their own blood supply, and is a major target of cancer research. Angiogenesis is believed to be the mechanism via which tumors get needed nutrients to grow and metastasize to other locations in the body. Antiangiogenic agents interfere with these processes and destroy or control tumors.

Angiogenesis is an attractive therapeutic target because it is a multistep process that occurs in a specific sequence, thus providing several possible targets for drug action. Antiangiogenic therapy may offer several advantages over conventional chemotherapy for the treatment of cancer.

The $\alpha_v\beta_3$ integrin antagonist agents have low toxicity in preclinical trials and development of drug resistance has not been observed (Folkman, J., Seminars in Medicine of the Beth Israel Hospital, Boston 333(26): 1757–1763, 1995). As angiogenesis is a complex process made up of many steps including invasion, proliferation and migration of endothelial cells, combination therapies will be effective in inhibiting angiogensis.

The phrase "therapeutically-effective" is intended to qualify the amount of each agent that will achieve the goal of improvement in neoplastic disease severity and the frequency of incidence over treatment of each agent by itself, while avoiding adverse side effects typically associated with alternative therapies.

A "therapeutic effect" relieves to some extent one or more of the symptoms of a neoplasia disease. In reference to the treatment of a cancer, a therapeutic effect refers to one or more of the following: 1) reduction in the number of cancer cells; 2) reduction in tumor size; 3) inhibition (i.e., slowing to some extent, preferably stopping) of cancer cell infiltration into peripheral organs; 4) inhibition, to some extent, of tumor growth; 5) relieving or reducing to some extent one or more of the symptoms associated with the disease; and/or 6) relieving or reducing the side effects associated with the administration of anticancer agents.

"Therapeutic effective amount" is intended to qualify the amount required to relieve to some extent one or more of the symptoms of a neoplasia disease. In reference to the treatment of a cancer, a therapeutic effect refers to one or more of the following: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anti-cancer agents.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the $\alpha_v\beta_3$ integrin antagonist compounds useful in the present invention are outlined in Schemes I–III. Both an explanation of, and the actual procedures for, the various aspects of the present invention are described where appropriate. The following Schemes and Examples are intended to be merely illustrative of the present invention, and not limiting thereof in either scope or spirit. Those with skill in the art will readily understand that known variations of the conditions and processes described in the Schemes and Examples can be used to synthesize the $\alpha_v\beta_3$ integrin antagonist compounds of the present invention.

Unless otherwise indicated all starting materials and equipment employed were commercially available.

Scheme I illustrates methodology useful for preparing the tetrahydropyrimidinobenzoic acid portion of the $\alpha_v\beta_3$ integrin antagonist which can be coupled to a gly-β-amino acid ester. Briefly, in Scheme I, 3,5-dihydroxybenzoic acid is converted to 3-amino-5-hydroxy-benzoic acid using the procedure described in *Austr. J. Chem.*, 34 (6), 1319–24 (1981). The product is reacted with ammonium thiocyanate in hot dilute hydrochloric acid to give 3-thiourea-5-hydroxybenzoic acid after normal work-up. This thiourea intermediate is converted to the S-methyl derivative by reaction with methyl iodide in ethanol at reflux. 1,3-diamino-2-hydroxypropane is reacted with this resulting intermediate in hot DMA. Upon cooling precipitate forms and the zwitterionic product is isolated by filtration. The HCl salt may be obtained by lyophilizing from dilute hydrochloric acid. Alternatively, the product may be isolated from the original reaction mixture by removing volatiles and concentrating. The resulting product is taken up in water and pH adjusted to about 5–7 where zwitterionic product precipitates and is isolated by filtration. The HCl salt may be obtained as previously stated or by simply dissolving in dilute hydrochloric acid and concentrating to a solid and drying.

SCHEME I

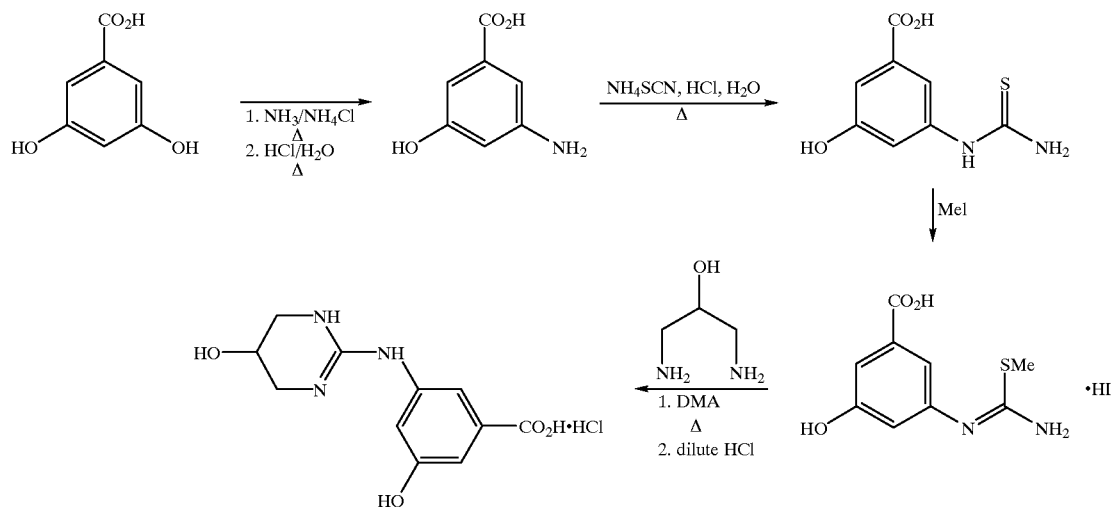

SCHEME IA

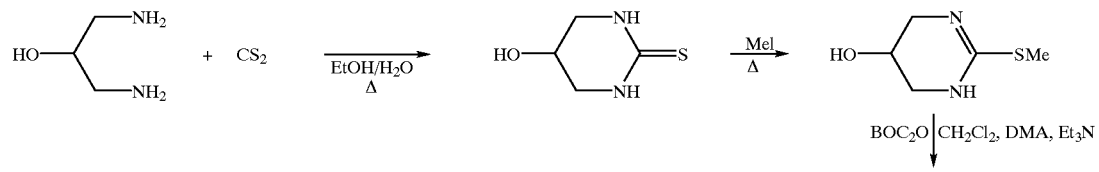

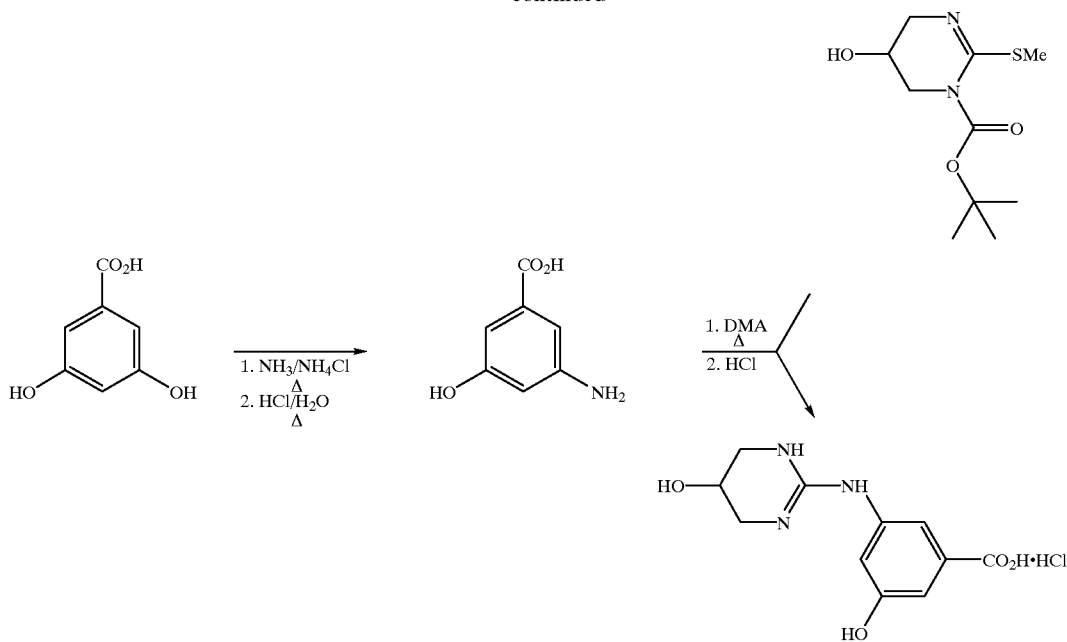

Scheme IA illustrates methodology useful for preparing the tetrahydropyrimidinobenzoic acid portion of the $\alpha_v\beta_3$ integrin antagonist which can be coupled to a gly-β-amino acid ester. Briefly, in Scheme IA 1,3-diamino-2-hydroxypropane is reacted with carbon disulfide in an appropriate solvent such as ethanol—water, refluxed, cooled, hydrochloric acid added, refluxed again, cooled and the product, 5-hydroxytetrahydropyrimidine-2-thione harvested by filtration and dried. This cyclic thiourea intermediate is converted to the S-methyl derivative by reaction of thione and methyl iodide in ethanol at reflux. The desired 2-methylthioether-5-hydroxypyrimidine hydroiodide is readily isolated by removing volatiles at reduced pressure. Thus, 2-methylthioether-5-hydroxypyrimidine hydroiodide in methylene chloride: DMA (about 10:1) and an equivalent of triethylamnine are cooled to about ice-bath temperature and an equivalent of di-tert-butyl dicarbonate (BOC anhydride) added. Conventional work-up gives the BOC-2-methylthioether-5-hydroxypyrimidine as an oil.

3,5-dihydroxybenzoic acid is converted to 3-amino-5-hydroxybenzoic acid using the procedure of *Aust. J. Chem.*, 34 (6), 1319–24 (1981).

The final desired product, 3-hydroxy-5-[(5-hydroxy-1,4,5,6-tetrahydro-2-pyrimidinyl)amino]benzoic acid hydrochloride salt, is prepared by reacting BOC-2-methylthioether-5-hydroxypyrimidine and 3-amino-5-hydroxy-benzoic acid in hot DMA. Upon cooling, a precipitate forms and zwitterionic product isolated by filtration. The HCl salt can be obtained by lyophilizing from dilute hydrochloric acid, for example.

SCHEME II

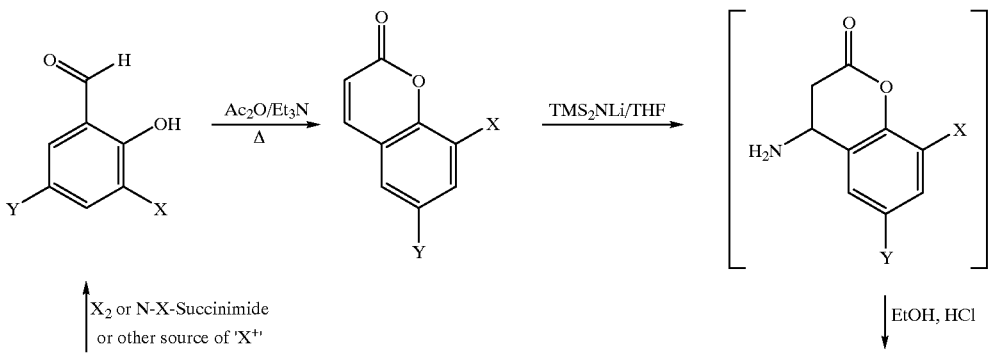

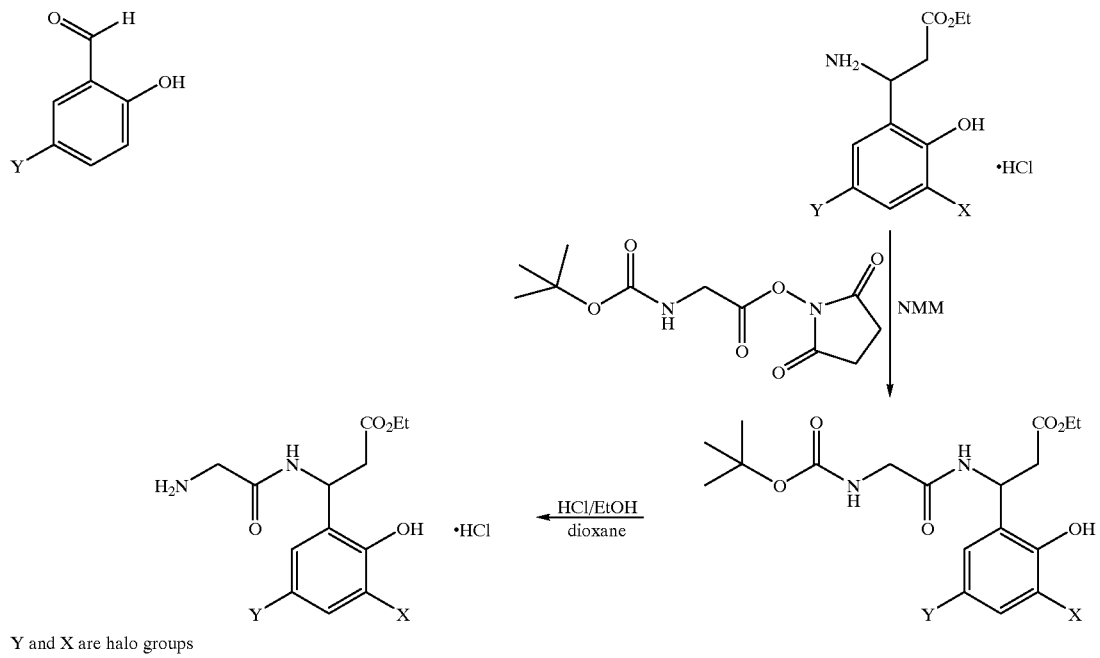

Y and X are halo groups

Scheme II illustrates methodology useful for preparing the ethyl N-gly-amino-3-(3,5-dihalo-2-hydroxy)phenyl propionate portion of the $\alpha_v\beta_3$ integrin antagonist which can be coupled to the tetrahydropyrimidinobenzoic acid moiety. Briefly, 3,5-halo substituted salicylaldehydes may be prepared by direct halogenation as, for example, would be the case where 5-bromosalicylaldehyde is slurried in acetic acid and an equivalent or more of chlorine is added to yield 3-chloro-5-bromo-2-hydroxybenzaldehyde. Some product precipitates and can be recovered by filtration. The remainder may be recovered by diluting the filtrate with water and isolating the precipitate. Combining the solids and drying gives 3-chloro-5-bromo-2-hydroxybenzaldehyde. 3-iodo-5-chlorosalicylaldehyde may be prepared by reacting 5-chlorosalicylaldehyde with N-iodosuccinimide in DMF and subjecting the reaction mixture to usual work-up conditions. 3-iodo-5-bromosalicylaldehyde may be prepared by reacting 5-bromosalicylaldehyde in acetonitrile with potassium iodide and chloramine T. Work-up gives a material that when treated with hexanes gives the desired 3-iodo-5-chlorosalicylaldehyde.

Coumarins are readily prepared from salicylaldehydes using a modified Perkin reaction (e.g., *Vogel's Textbook of Practical Organic Chemistry*, 5th Ed., 1989, p. 1040,). The halo-substituted coumarins are converted to 3-aminohydrocoumarins (see J. G. Rico, *Tett. Let.,* 1994, 35, 6599–6602) which are readily opened in acidic alcohol to give 3-amino-3-(3,5-halo-2-hydroxy)phenyl propanoic acid esters.

3-amino-3-(3,5-halo-2-hydroxy)phenyl propanoic acid esters are converted to N-gly-3-amino-3-(3,5-halo-2-hydroxy)phenyl propanoic acid esters by reaction of Boc-N-gly-N-hydroxysuccinimide to give Boc-N-gly-3-amino-3-(3,5-halo-2-hydroxy)phenyl propanoic acid esters that are converted to HX salts of N-gly-3-amino-3-(3,5-halo-2-hydroxy)phenyl propanoic acid esters (wherein X is a halo group) for example, by removal of the BOC-protecting group using HCl in ethanol.

The amino acid compounds used in preparing the $\alpha_v\beta_3$ integrin antagonist compounds of the present invention can be prepared according to the procedures set forth herein and below and according to the methodology described and claimed in co-pending U.S. Ser. No. 60/076,710 filed Mar. 4, 1998.

SCHEME III

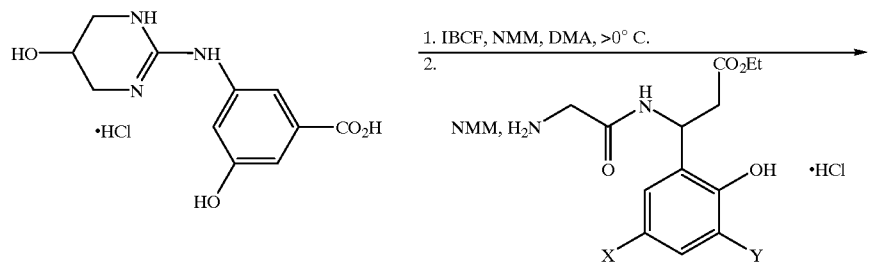

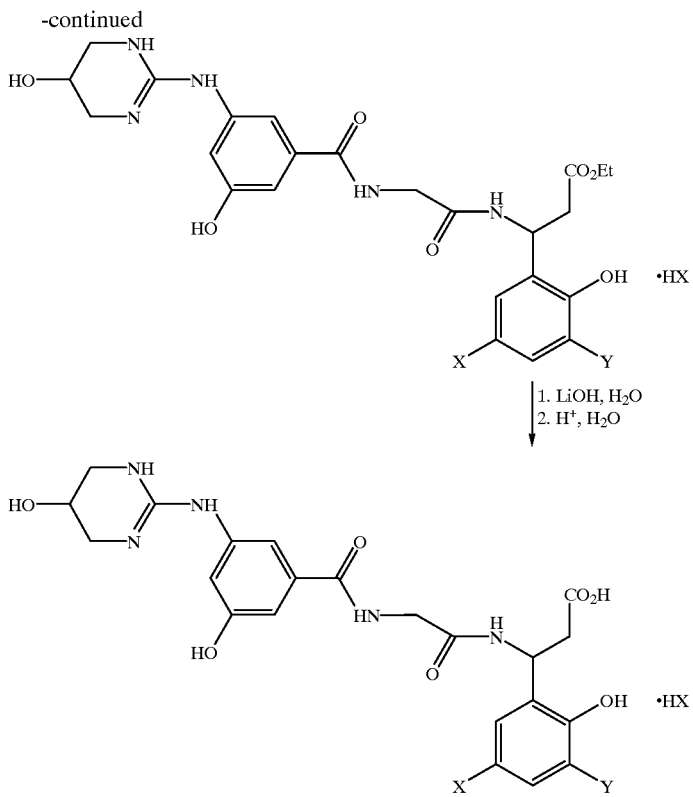

Y and X are halo groups

Scheme III is illustrative of methodology useful for preparing various α,β₃ integrin antagonist compounds of the present invention. 3-Hydroxy-5-[(1,4,5,6-tetrahydro-5-hydroxy-2-pyrimidinyl)amino]benzoic acid is activated to coupling using known methods. Thus, after dissolving in a suitable solvent such as DMA an equivalent of NMM is added. The reaction mixture is cooled to ice-bath temperatures and IBCF added. To the mixed anhydride intermediate is added the gly-β-amino acid ester and NMM. Upon completion of the reaction the product is purified by prep hplc and the ester hydrolyzed to the acid by treating with a base, such as LiOH in a suitable solvent (dioxane/water or acetonitrile/water). Alternatively, a suitable acid, such as TFA can be used. The product is isolated by prep hplc or by isolating the zwitterion at pH 5–7 and converting to the desired salt by standard procedures.

EXAMPLE A

Step 1

Preparation of

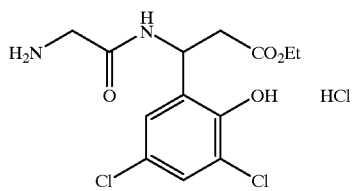

Preparation of

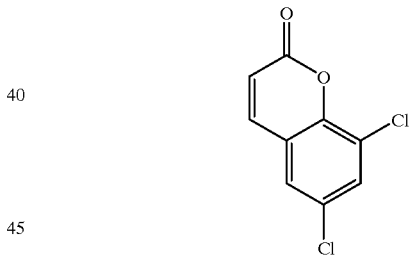

To a 2 L round bottom flask fitted with a mechanical stirrer and condenser was added 3,5-dichlorosalicylaldehyde (200 g, 1.05 mol, 1 equiv.), acetic anhydride (356 g, 3.49 mol) and triethylamine (95.0 g, 0.94 mol, 0.90 equiv.). The reaction solution was heated at reflux overnight. The dark brown reaction mixture was cooled to 50° C. and water (1 L) added with stirring. After one hour the mixture was filtered and the filtrate combined with EtOH (1 L). This mixture was heated to 45° C. for one hour, cooled to room temperature, filtered and the solid (fraction A) washed with EtOH (0.5 L). The combined EtOH solutions were concentrated by rotary evaporation to an oil (fraction B). The solid from fraction A was dissolved in methylene chloride (1.5 L) and the resulting solution passed through a pad of silica gel (1300 mL volume). The resulting dark brown solution was concentrated to an oil that was triturated with hexanes (1.3 L) to give a solid that was isolated by filtration and washed (hexanes) to give substantially pure 6,8-dichlorocoumarin (163 g). A further 31 g of product was obtained by treating the oil, fraction B, in a similar fashion; the oil was dissolved in methylene chloride (0.5 L) passed through a silica pad (0.5 L volume) and triturated with hexanes. The total isolated yield was 194 g or 86% yield of the brown solid.

MS and NMR were consistent with the desired structure.

Step 2
Preparation of

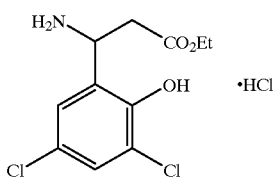

To a 3-neck 2 L round bottom flask fitted with a mechanical stirrer was added 6,8-dichlorocoumarin (160 g, 0.74 mol) (prepared in Step 1) and dry THF (375 mL, Aldrich Sure Seal). The resulting mixture was cooled to −40° C. (dry ice/acetone bath) and lithium bis(trimethylsilyl)amide (0.80 mol 800 mL of 1M in THF) added while maintaining temperature below −40° C. After the completion of the addition the cooling bath was removed. After 0.5 hour the mixture had warmed to −5° C. The reaction was quenched by addition of a solution of HCl (0.5 L of 4M in dioxane) in EtOH (1.25 L). The temperature was maintained below 0° C. overnight. The reaction mixture was concentrated to about one-half its original volume and partitioned between EtOAc (3 L) and water (2 L). The organic layer was washed with aqueous HC (3×1 L 0.5 N HCl). The pH of the combined aqueous layers was adjusted to about 7 by addition of 10% aqueous NaOH and extracted with methylene chloride (3×2 L). The combined organic layers were dried (MgSO$_4$), filtered, and 4M HCl in dioxane (210 mL) added with stirring. Upon completion of precipitation the solid was removed by filtration. The filtrate was concentrated to a small volume and methyl t-butyl ether added. The solid obtained was combined with the initially formed solid and the combined product was washed with methyl t-butyl ether, isolated by filtration and dried (vacuum oven over a weekend) to obtain the desired product (172 g, 74% yield).

MS and NMR were consistent with the desired structure.

Step 3
Preparation of

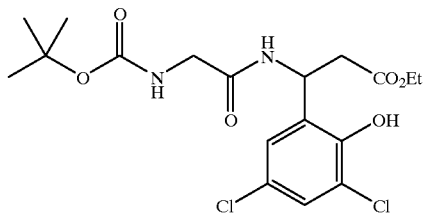

To a flame-dried round bottom flask (0.5 L) equipped with magnetic stir bar was added N-t-Boc-glycine N-hydroxysuccinimide ester (Sigma, 15.0 g, 0.055 mol), dry DMF (Aldrich Sure Seal, 200 mL) and the product from Step 2 (21.67 g, 0.055 mol) under an inert atmosphere (Ar). The reaction mixture was cooled to approximately 0° C. (salt-ice bath) and N-methylmorpholine (5.58 g, 0.056 mole) and a catalytic amount of DMAP added and the reaction allowed to proceed overnight. The reaction mixture was concentrated to a slush, and partitioned between EtOAc (0.4 L) and aqueous base (2×0.2 L, aqueous saturated NaHCO$_3$). The organic layer was washed consecutively with aqueous citric acid (2×0.2 L, 10% w/v), again with aqueous sodium bicarbonate (2×0.2 L), brine and dried (Na$_2$SO$_4$). Volatiles were removed under vacuum at 55° C. to give an oil (22.5 g, 92% yield) that solidified on standing.

MS and NMR were consistent with the desired structure.

Step 4
Preparation of

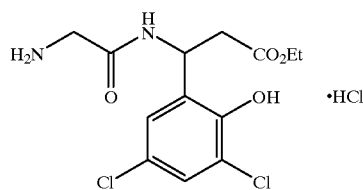

The product obtained in Step 3 was de-protected to give the amine hydrochloride salt using the following procedure. To the product from Step 3 (14.0 g, 0.032 mole) in a flame-dried round bottom flask (0.1 L) with stir bar was added dry dioxane (40 mL). To this was added 4.0 N HCl in dioxane (2 equiv., 6.32 mL) at 0° C. and the reaction allowed to proceed until gas evolution ceased and the reaction was complete. Volatiles were removed under vacuum and the residue triturated with diethyl ether (50 mL). Solids were collected by filtration and washed with ether and dried to give the desired product (12.5 g).

MS and NMR were consistent with the desired structure.

EXAMPLE B

Preparation of

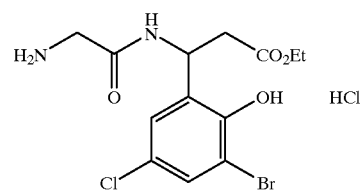

Step 1
Preparation of

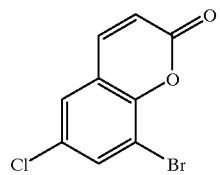

To a suspension of 3-bromo-5-chlorosalicylaldehyde (175.0 g, 743.2 mmol) in acetic anhydride (280.5 mL, 3.0 mol) was added triethylamine (103.6 mL, 743.2 mmol). The reaction solution was heated at reflux for 4.5 hours. The solution was cooled and concentrated in vacuo. To the brown residue was added absolute ethanol (730 mL). The mixture was stored at 0° C. for 14 hours. The brown solid was collected by filtration and washed with cold ethanol. The solid was dried in vacuo to give the desired product (123.0 g, 64% yield). $^1$H NMR was consistent with the proposed structure.

Step 2
Preparation of

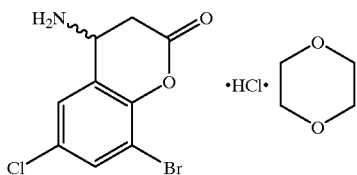

To a suspension of the coumarin (40.0 g, 154.1 mmol) in THF (400 mL) at −76° C. was added, dropwise with stirring, lithium bis(trimethylsilyl)amide (154.1 mL of a 1M solution in THF). The addition was completed in 10 minutes. The reaction mixture was then stirred for 5 minutes, warmed to −20° C. and stirred for 15 minutes. To this solution was added acetic acid (9.25 g, 154.1 mmol) in THF (28 mL) over 5 minutes. The mixture was warmed to room temperature and volatiles were removed in vacuo. The residue was dissolved in ether (850 mL), washed with saturated aqueous NaHCO$_3$ (2×100 mL), brine (2×40 mL) and dried (MgSO$_4$). The ether solution was concentrated to about 160 mL and cooled to 0° C. To this suspension was added 4M HCl in dioxane (56.3 mL, 225 mmol) and the mixture was stirred at 0° C. for 30 minutes. The suspension was filtered and the filter cake washed with ether. The solid was dried in vacuo to give the desired product as the HCl salt, dioxane solvate, (45.0 g). $^1$H NMR was consistent with the proposed structure.

Step 3
Preparation of

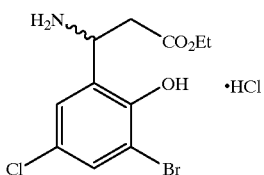

To a suspension of the lactone (142.2 g, 354.5 mmol) in absolute ethanol (533 mL) was added 4M HCl in dioxane (157.8 mL, 631.1 mmol) over 10 minutes. The reaction mixture was stirred at room temperature for 2.5 hours. Volatiles were removed in vacuo. The residue was dissolved in ethyl acetate (450 mL) and the solution kept at 0° C. for 15 hours. The tan precipitate was collected by filtration and washed with cold ethyl acetate. The solid was dried in vacuo to give the desired product as the hydrochloride salt (100.4 g, 79% yield). $^1$H NMR was consistent with the proposed structure.

Step 4
Preparation of

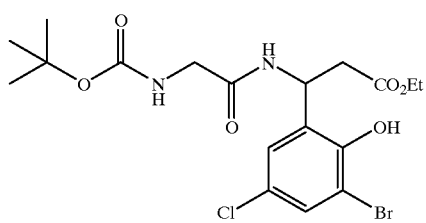

To a flame-dried round bottom flask (0.1 L) equipped with magnetic stir bar was added N-t-Boc-glycine N-hydroxysuccinimide ester (Sigma, 2.72 g, 0.010 mol), dry THF (Aldrich Sure Seal, 50 mL) and the product from Step 3 (3.10 g, 0.01 mole, vacuum desiccated overnight over P$_2$O$_5$) under an inert atmosphere (Ar). The reaction mixture was cooled to approximately 0° C. (salt-ice bath) and triethylamine (1.01 g, 0.010 mole) was added. The reaction was allowed to proceed overnight. The reaction mixture was concentrated to a semi-solid and worked up in a fashion similar to Example A, Step 3. Volatiles were removed from the organic layer under vacuum at 55° C. to give an oil (4 g, 83% yield) that solidified on standing.

MS and NMR were consistent with the desired structure.

Step 5
Preparation of

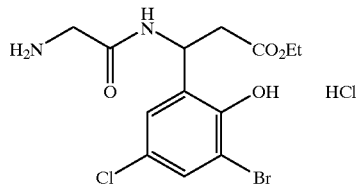

The product obtained in Step 4 was de-protected to give the amine hydrochloride salt using the following procedure. To the product from Step 4 (4.0 g, 0.0084 mole) in a flame-dried round bottom flask (0.1 L) with stir bar was added dry dioxane (20 mL). To this was added 4.0 N HCl in dioxane (20 mL) and the reaction allowed to proceed until gas evolution ceased and the reaction was complete (about one hour). Volatiles were removed under vacuum and the residue triturated with diethyl ether (50 mL). Solids were collected by filtration and washed with ether and dried to give a light brown solid (2.7 g, 78% yield).

MS and NMR were consistent with the desired structure.

EXAMPLE C

Preparation of

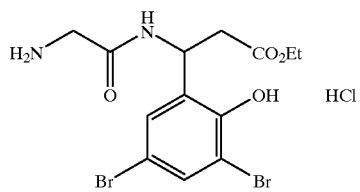

Step 1

To a suspension of 3,5-dibromosalicylaldehyde (100 g, 357 mmol) in acetic anhydride (164.8 mL, 1.8 mol) was added triethylamine (45 mL, 375 mmol). The reaction solution was heated overnight at reflux under argon. The solution was cooled to room temperature and a solid mass formed. The dark brown reaction mixture was washed with hot hexanes (3×300 mL) and aqueous saturated sodium bicarbonate. The resulting solid was dissolved in EtOAc (2 L) and washed with water. The organic layer was dried (sodium sulfate) and concentrated to give a brown solid that was collected by filtration. The solid was dried in vacuo to give substantially pure 6,8-dibromocoumarin (94.2 g, 87% yield).

MS and $^1$H NMR were consistent with the desired structure.

Step 2

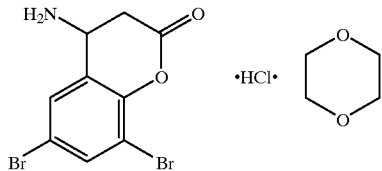

To 6,8-dibromocoumarin (20.0 g, 0.066 mol) (prepared in Step 1) in THF (100 mL) at −78° C. was added dropwise with stirring lithium bis(trimethylsilyl)amide (66 mL of a 1M solution in THF). The addition was completed in 10 minutes. The reaction mixture was then stirred for 5 minutes, warmed to 0° C. and stirred for 15 minutes. To this solution was added acetic acid (3.95 g) over one minute. The mixture was warmed to room temperature and volatiles were removed in vacuo. The residue was dissolved in hexanes (500 mL), washed with saturated aqueous NaHCO$_3$ (2×100 mL) and dried (Na$_2$SO$_4$). The organic solution was concentrated to give an oil that was immediately taken up in diethyl ether (400 mL) and 4M HCl in dioxane (30 mL) was added with stirring at 0° C. for 30 minutes. Excess HCl was removed in vacuo, the suspension filtered and the filter cake washed with ether. The solid was dried in vacuo to give the desired product as the HCl salt, dioxane solvate (19.9 g).

MS and $^1$H NMR were consistent with the desired structure.

Step 3

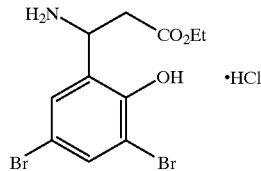

The lactone prepared in Step 2 above (15 g) was dissolved in absolute ethanol (400 mL) and anhydrous HCl gas was passed through for one minute. The reaction mixture was stirred at room temperature for 2.5 hours. RPHPLC showed complete reaction. The volatiles were removed in vacuo to give a dark residue. The residue was triturated with diethyl ether (500 mL) and the mixture stirred overnight. The tan precipitate was collected by filtration and washed with diethyl ether. The solid was dried in vacuo to give the desired product as the hydrochloride salt (15.2 g).

MS and $^1$H NMR were consistent with the desired structure.

Step 4

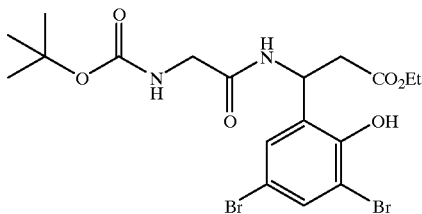

To a flame-dried round bottom flask (0.2 L) equipped with magnetic stir bar was added N-t-Boc-glycine N-hydroxysuccinimide ester (Sigma, 8.1 g, 0.030 mol), dry DMF (Aldrich Sure Seal, 50 mL) and the product of Step 3 (12 g, 0.03 mole, vacuum desiccated overnight over P$_2$O$_5$) under an inert atmosphere (Ar). The reaction mixture was cooled to approximately −0° C. (salt-ice bath) and N-methyl morpholine (3.03 g, 0.030 mole) and catalytic DMAP added. The reaction was allowed to proceed overnight warming to room temperature. The reaction mixture was concentrated to a semi-solid and worked up in a fashion similar to Example A, Step 3. Volatiles were removed from the organic layer under vacuum at 55° C. to give an oil (15.7 g, 93% yield) that solidified on standing.

MS and NMR were consistent with the desired structure.

Step 5

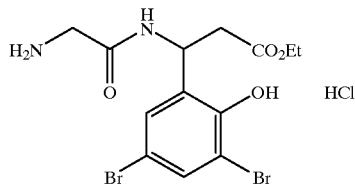

The product obtained in Step 4 was deprotected to give the amine hydrochloride salt using the following procedure. To the product from Step 4 (13.0 g, 0.0084 mole) in a flame-dried round bottom flask (0.1 L) with stir bar was added dry dioxane (40 mL). To this was added 4.0 N HCl in dioxane (30 mL) and the reaction allowed to proceed until gas evolution ceased and the reaction was complete (about one hour). The volatiles were removed under vacuum and the residue triturated with diethyl ether (50 mL). Solids were collected by filtration and washed with ether and dried to give a solid (10.6 g, 93% yield).

MS and NMR were consistent with the desired structure.

EXAMPLE D

Preparation of

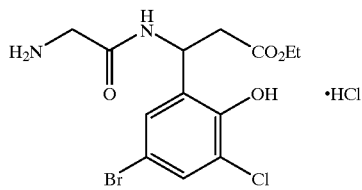

Step 1

Preparation of 3-chloro-5-bromosalicylaldehyde

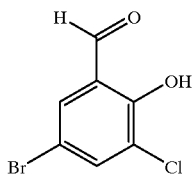

To a 5 L round bottom flask fitted with a mechanical stirrer and gas addition tube was added 5-bromosalicylaldehyde (495 g, 2.46 mol) and acetic acid at ambient temperature to form a slurry. To this mixture was added chlorine gas at a moderate rate until a slight molar excess of chlorine (183 g, 1.05 mol) had dissolved. After the addition was stopped the reaction allowed to proceed overnight. The solid formed was recovered by filtration and the filtrate diluted into water (2.5 L). The mixture was stirred vigorously for 20 minutes, the product collected by filtration and washed with water. The combined solids were vacuum dried to give the desired 3-chloro-5-bromosalicylaldehyde (475 g, 82% yield).

MS and $^1$H NMR were consistent with the desired structure.

Step 2

Preparation of 6-bromo-8-chlorocoumarin

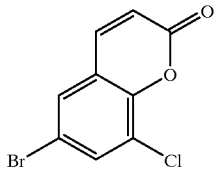

To a 5 L round bottom flask fitted with a mechanical stirrer and condenser was placed 3-chloro-5-bromosalicylaldehyde (554.1 g, 2.35 mol, 1 equiv.), acetic anhydride (1203 g, 11.8 mol, 5 equiv.) and triethylamine (237.4 g , 2.35 mol, 1 equiv.). The reaction solution was heated at reflux (131–141° C.) overnight. The dark brown reaction mixture was cooled to 50° C. and ice (2 L) added (ice-bath cooling) with stirring. After one hour the mixture was filtered and the filtrate combined with EtOH (1 L). To this mixture was added EtOH (300 mL) and the reaction mixture stirred for one hour. The precipitate that formed was collected by filtration and washed with water: EtOH (3×1.3 L), vacuum and dried then dried on a fluid-bed drier. The total isolated yield is 563 g or 92%.

MS and $^1$H NMR were consistent with the desired structure.

Step 3

Preparation of 3-amino-3-(2-hydroxy-3-chloro-5-bromo)phenyl propanoic acid ethyl ester

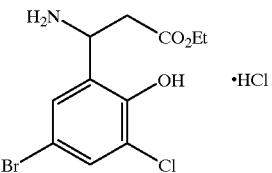

To a 3-neck 5 L round bottom flask fitted with a mechanical stirrer was added 6-bromo-8-chlorocoumarin (300 g, 1.16 mol) (prepared in Step 2) and dry THF (900 mL, Aldrich Sure Seal). The resulting mixture was cooled to less than −45° C. (dry ice/acetone bath) and lithium bis (trimethylsilyl)amide (0.80 mol , 800 mL of 1M in THF and 0.6 L in hexanes, 1.2 equivalents) added while maintaining temperature below −45° C. for 0.5 hour. In a separate 5 L flask EtOH (2.5 L) and HCl (4 N HCl in dioxane, 1 L) were combined at −15° C. The coumarin reaction was quenched by addition of the cooled HCl/EtOH solution. After 0.5 hour the resulting reaction mixture temperature was −8.3° C. The reaction mixture was kept at 0° C. overnight, concentrated to about 2.5 L and partitioned between EtOAc (3 L) and water (4 L). The organic layer was washed with aqueous HCl (4×1.2 L, 0.5 N HCl). The pH of the combined aqueous layers was adjusted to about 8 by addition of 10% aqueous NaOH and extracted with methylene chloride (1×7 L and 3×2 L). The combined organic layers were dried (MgSO$_4$, 900 g), filtered, and 4M HCl in dioxane (400 mL) added with stirring. Upon completion of precipitation the solid was removed by filtration. The mixture was concentrated to 2.5 L, hexanes added (2.5 L) and the precipitate isolated by filtration. The filter cake was washed with methylene chloride/hexanes (1:2), suction dried and vacuum oven dried at 40° C. to obtain the desired product (251 g, 60% yield).

MS and $^1$H NMR were consistent with the desired structure.

Step 5

Preparation of

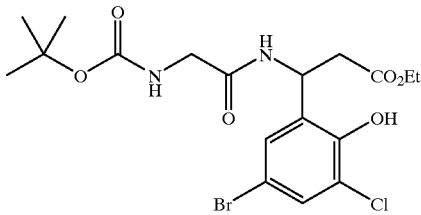

The above compound was prepared using essentially the same procedure and relative quantities as specified for its isomer in Example B, Step 4.

MS and $^1$H NMR were consistent with the desired structure.

Step 6

Preparation of

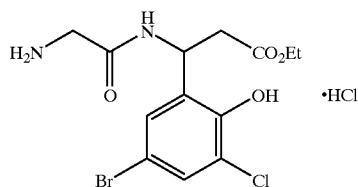

This compound was prepared using essentially the same procedure and relative quantities as specified for its isomer in Example B. Step 5.

MS and $^1$H NMR were consistent with the desired structure.

EXAMPLE E

Preparation of

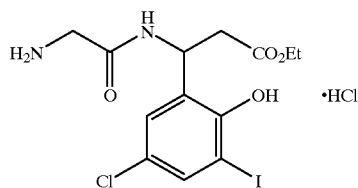

Step 1

Preparation of 3-iodo-5-chlorosalicylaldehyde

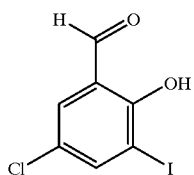

N-Iodosuccinimide (144.0 g, 0.641 mole) was added to a solution of 5-chlorosalicylaldehyde (100 g, 0.638 mole) in dimethylformamide (400 mL). The reaction mixture was stirred for 2 days at room temperature. Additional N-iodosuccinimide (20.0 g) was added and the stirring was continued for an additional 2 days. The reaction mixture was diluted with ethyl acetate (1 L), washed with hydrochloric acid (300 mL, 0.1N), water (300 mL), sodium thiosulfate (5%, 300 mL), brine (300 mL), dried (MgSO$_4$) and was concentrated to dryness to afford the desired aldehyde (162 g, 90% yield) as a pale yellow solid.

MS and NMR were consistent with the desired structure.

Step 2

Preparation of 6-chloro-8-iodocoumarin

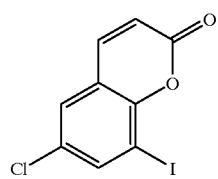

A mixture of 3-iodo-5-chlorosalicylaldehyde (100 g, 0.354 mole), acetic anhydride (300 mL) and triethylamine (54 mL) was heated at reflux for 18 hours. Upon cooling, the desired coumarin precipitated as a dark brown crystalline material. This was filtered, washed with hexane/ethyl acetate (4:1, 200 mL), and was air dried. Yield: 60 g (55%).

MS and $^1$H NMR were consistent with the desired structure.

Step 3

Preparation of (R,S)-4-amino-3,4-dihydro-6-chloro-8-iodocoumarin hydrochloride

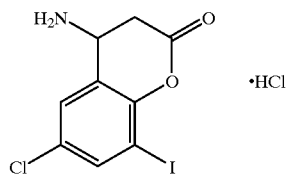

Lithium hexamethyldisilazane (21.62 mL, 1 M, 21.62 mmol) was added to a solution of 6-chloro-8-iodocoumarin (6.63 g, 21.62 mmol) in tetrahydrofuran (100 mL) at −78° C. The reaction mixture was stirred at this temperature for 30 minutes, then at 0° C. for 1 hour. Acetic acid (1.3 g, 21.62 mmol) was added to the reaction mixture. The reaction mixture was poured into ethyl acetate (300 mL) and saturated sodium carbonate (200 mL) solution. The organic layer was separated, washed with brine (200 mL), dried (MgSO$_4$), and was concentrated to afford a residue. The residue was added to anhydrous ether (200 mL) followed by dioxane/HCl (4N, 30 mL) at 0° C. The reaction mixture was stirred for 1 hour at room temperature, filtered, and was dried in vacuo to afford the desired product (4.6 g, 59% yield) as a powder. (RPHPLC: Rf 6.8 minutes; Gradient 10% acetonitrile −90% acetonitrile over 15 minutes then to 100% acetonitrile over the next 6 minutes. Both water and acetonitrile contain 0.1% TFA. Vydac C18 protein peptide column, 2 mL/minutes flow rate, monitored at 254 nm).

MS and $^1$H NMR were consistent with the desired structure.

Step 4

Preparation of (R,S)-Ethyl 3-amino-3-(5-chloro-2-hydroxy-3-iodo)phenyl propionate hydrochloride

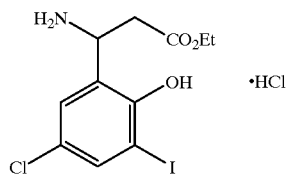

Hydrogen chloride gas was bubbled into a solution of 4-amino-3,4-dihydro-6-chloro-8-iodocoumarin hydrochloride (22.0 g, 61.09 mmol) in ethanol (250 mL) keeping the reaction mixture at 0–10° C. till saturation. After 6 hours at reflux, most of the solvent was removed by distillation. The cooled residue was added to anhydrous ether and was stirred for 2 hours. The initial gum turned into a crystalline material. The crystalline product was filtered and was dried to afford the desired product (20 g, 81% yield) as a off-white crystalline powder. (Rf 7.52 minutes, conditions as Step 3).

MS and $^1$H NMR were consistent with the desired structure.

Step 5

Preparation of (R,S)-ethyl 3-(N-BOC-gly)-amino-3-(5-chloro-2-hydroxy-3-iodo)phenyl propionate

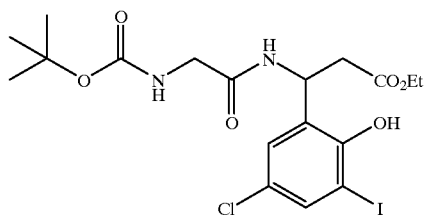

A mixture of BOC-gly (2.16 g, 12.31 mmol), HOBT (1.67 g, 12.31 yield), EDCl (2.36 g, 12.31 mmol) and DMF (50 mL) was stirred at 0° C. for 1 hour. Ethyl 3-amino-3-(5-chloro-2-hydroxy-3-iodo)propionate hydrochloride (5.0 g, 12.31 mmol) was added to the reaction mixture followed by triethylamine (3.5 mL). The reaction mixture was stirred for 18 hours at room temperature. DMF was removed in vacuo and the residue was partitioned between ethyl acetate (300 mL) and sodium bicarbonate (200 mL). The organic layer was washed with hydrochloric acid ($_1$N, 100 mL), brine (200 mL), dried (MgSO$_4$) and was concentrated to afford the desired product as a solid (6 g, 93% yield).

MS and $^1$H NMR were consistent with the desired structure.

Step 6

Preparation of (R,S)-ethyl 3-(N-gly)-amino-3-(5-chloro-2-hydroxy-3-iodo)phenyl propionate hydrochloride

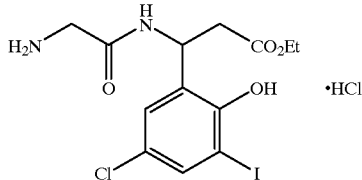

Dioxane/HCl (4N, 20 mL) was added to ethyl 3-(N-BOC-gly)-amino-3-(5-chloro-2-hydroxy-3-iodo)propionate (6.0 g, 11.39 mmol) at 0° C. and was stirred at room temperature for 3 hours. The reaction mixture was concentrated, and concentrated once more after addition of toluene (100 mL). The residue obtained was suspended in ether and was filtered and dried to afford the desired product as a crystalline powder (5.0 g, 95% yield). (RPHPLC: Rf 8.3 minutes, conditions as in Step 3).

MS and $^1$H NMR were consistent with the desired structure.

EXAMPLE F

Preparation of

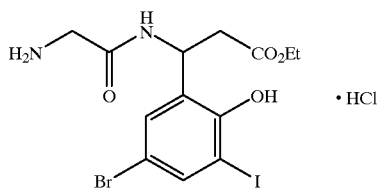

Step 1

Preparation of 3-iodo-5-bromosalicylaldehyde

To a solution of 5-bromosalicylaldehyde (20.0 g, 0.1 mole) and potassium iodide (17 g , 0.1 mole) in acetonitrile (150 mL) and water (50 mL) in a 500 mL round bottom flask with magnetic stirrer was added chloramine T (23 g, 0.1 mole). The mixture was allowed to react for one hour. The reaction mixture was partitioned between hydrochloric acid (10%, 200 mL) and ethyl acetate. The organic layer was dried (Na$_2$SO$_4$), filtered and concentrated in vacuo. To the residue was added hexanes and the reaction mixture heated to 50° C. for 15 minutes. The undissolved material was removed by filtration. The filtrate was concentrated in vacuo to leave canary yellow 3-iodo-5-bromosalicylaldehyde (26 g).

MS and $^1$H NMR were consistent with the desired structure.

Step 2

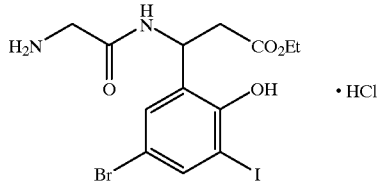

The above compound was prepared using essentially the same procedure of Example E, Steps 2–6 where in Step 2, an equivalent amount of product from Step 1, 3-iodo-5-bromo-salicylaldehyde, was substituted for 3-iodo-5-chlorosalicylaldehyde.

MS and $^1$H NMR were consistent with the desired structure.

EXAMPLE H

Preparation of

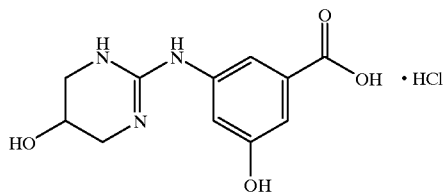

Step 1

Ethanol (375 mL) and deionized water (375 mL) were added to a 2 L 3-neck round bottom flask fitted with a mechanical stirrer, Claisen adapter, addition funnel, reflux condenser and thermocouple. 1,3- diamino-2-hydroxypropane (125.04 g, 1.39 mol) (Aldrich) was added to the reaction flask and stirred to dissolve. Carbon disulfide (84 mL, 1.39 mol) was added in a drop-wise fashion via addition funnel at 25–33° C. over a 35 minute period to afford a milky-white mixture. The temperature was maintained with an ice bath. The reaction mixture was refluxed at 73.4° C. for two hours to afford a yellow solution. The reaction mixture was cooled with an ice bath to 25° C. and concentrated HCl (84 mL) was added in drop-wise fashion while maintaining the temperature at 25–26° C. The reaction mixture was refluxed for 21 hours at 78.4° C. The reaction solution was cooled to 2° C. and product collected via vacuum filtration. The white solid was washed 3 times with ice bath chilled ethanol : water (1:1) (50 mL) and dried in vacuo at 40° C. to afford 5-hydroxytetrahydropyrimidine-2-thione (63.75 g, 34.7% yield) as a white solid.

MS and NMR were consistent with the desired structure.

Step 2

5-Hydroxytetrahydropyrimidine-2-thione (95 g, 0.72 mol) prepared in Step 1, absolute ethanol (570 mL), and methyl iodide (45 mL, 0.72 mol) were added to a 2 L round bottom flask fitted with a mechanical strirrer and thermocouple. The reaction mixture was refluxed at 78° C. for 5 hours and then cooled to room temperature. The reaction mixture was concentrated in vacuo to afford a white solid (194.72 g). The white solid was triturated 3 times with ethyl ether (500 mL ) and dried in vacuo to afford 2-methylthioether-5-hydroxypryrimidine hydroiodide (188.22 g, 95.4% yield) as a white solid.

MS and $^1$H NMR were consistent with the desired structure.

Step 3

2-Methyl thioether-5-hydroxypyrimidine hydroiodide (150.81 g, 0.55 mol), methylene chloride (530 mL), dimethylacetamide (53 mL) and triethylamine (76.7 mL, 0.55 mol) were added to a 2 L 3-neck round bottom flask fitted with reflux condenser, mechanical stirrer and a static atmosphere of nitrogen. The mixture was cooled with an ice bath and di-tert-butyl dicarbonate (120.12 g, 0.55 mol) was added at 4° C. The reaction mixture was heated at 42.5° C. for 18 hours to afford a light yellow solution. The reaction solution was transferred to a 2 L separatory funnel and washed 3 times with DI water (200 mL), dried with MgSO$_4$, filtered and concentrated in vacuo to afford Boc-2-methylthioether-5-hydroxypyrimidine (134.6 g, 99.35% yield) as a light yellow viscous oil.

MS and $^1$H NMR were consistent with the desired structure.

Step 4

Boc-2-methylthioether-5-hydroxypyrimidine (50.3 g, 0.204 mol), 3-amino-5-hydroxybenzoic acid (Aust. J. Chem. (1981) 34(6), 1319–24) (25.0 g, 0.1625 mole) and 50 mL anhydrous DMA were heated at 100° C. with stirring for 2 days. A slurry precipitate resulted. The reaction was cooled to room temperature and the precipitate was filtered, washed with CH$_3$CN, then ethyl ether and dried. This solid was slurried in H$_2$O and acidified with concentrated HCl resulting in a solution. This was frozen and lyophilized to yield the desired product as a white solid (14.4 g).

MS and $^1$H NMR were consistent with the desired structure.

EXAMPLE I

Preparation of

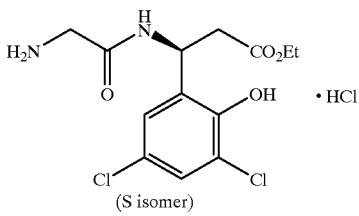

(S isomer)

Step 1
Preparation of Reformatsky Reagent

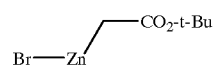

A 4-L flask fitted with a condenser, temperature probe and mechanical stirrer was charged with Zn metal (180.0 g, 2.76 mol, −30–100 mesh) and THF (1.25 L). While stirring, 1,2-dibromoethane (4.74 mL, 0.05 mol) was added via syringe [alternatively, TMS Cl (0.1 equivalent) at room temperature for one hour can be substituted]. After inert gas purge (3 N$_2$/vacuum cycles) the suspension of zinc in THF was heated to reflux (65° C.) and maintained at this temperature for 1 hour. The mixture was cooled to 50° C. before charging tert-butyl bromoacetate (488 g, 369 mL, 2.5 mol) via 50 mL syringe and syringe pump (delivery set to 4.1 mL/minutes) over 1.5 hours. Reaction temperature of 50°+/−5° C. was maintained throughout the addition. The reaction mixture was allowed to stir at 50° C. for one hour after the addition was complete. Subsequently, the mixture was allowed to cool to 25° C. and the precipitated product allowed to settle. The THF mother liquor was decanted into a 2-L round bottom flask using a coarse fritted filter stick and partial vacuum transfer (20 mm Hg). This removed about 65% of the THF from the mixture. 1-Methyl-2-pyrrolidinone (NMP, 800 mL) was added and agitation resumed for 5 minutes. The reaction mixture can be filtered to remove any remaining zinc. Analysis indicated a titer of desired Reformatsky reagent 1.57 M with a molar yield of 94%. Alternatively, the solid reagent can be isolated by filtration from the original reaction mixture. The cake can be washed with THF until a white solid is obtained and dried under N$_2$ to obtain the desired product as a mono THF solvate that may be stored at −20° C. (desiccated) for extended periods. Typical recoveries are 85–90%.

Step 2
2A. Preparation of

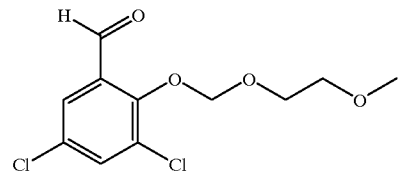

Potassium carbonate (powder, oven dried at 100° C. under vacuum, 8.82 g, 60 mmoles) was added to a solution of 3,5-dichlorosalicylaldehyde (11.46 g, 60 moles) in DMF (40 mL) at room temperature to give a bright yellow slurry. MEMCl (neat, 7.64 g, 61 mmoles) was then added while maintaining the bath temperature at 20° C. The mixture was then stirred at 22° C. for 6 hours and MEMCl (0.3 g, 2.4 mmoles) was added. The mixture was stirred for another 0.5 hour and the reaction mixture poured into cold water (200 mL) to precipitate the product. The slurry was filtered on a pressure filter and the cake was washed with water (2×50 mL) and was dried under N₂/vacuum to afford the product (14.94 g, 89%) as a off white solid. $^1$H NMR (CDCl₃, TMS) 3.37 (s, 3H), 3.54 to 3.56 (m, 2H), 3.91 to 3.93 (m, 2H), 5.30 (s, 2H), 7.63 (d, 1H), 7.73 (d, 1H), 10.30 (s, 1H); $^{13}$C NMR (CDCl₃, TMS) d (ppm):59.03, 70.11, 99.57, 126.60, 129.57, 130.81, 132.07, 135.36, 154.66, 188.30. DSC: 48.24° C. (endo 90.51 J/g); Microanalytical: calcd for $C_{11}H_{12}Cl_2O_4$: C, 47.33%; H, 4.33%; Cl, 25.40%; found: C, 47.15%; H, 4.26%; Cl, 25.16%.

2B. Preparation of

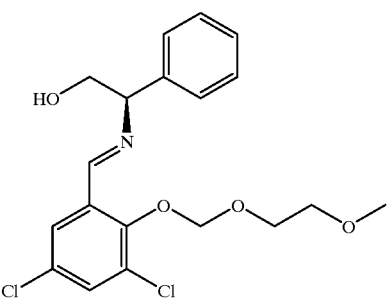

The product from Step 2A (35.0 g, 0.125 mol) was charged in a 1-L 3-neck round bottom flask fitted with a mechanical stirrer and an addition funnel followed by addition of THF (200 mL).The solution was stirred at 22° C. and (S)-phenylglycinol (17.20 g, 0.125 mol) was then added at once. After 30 minutes at 22° C., MgSO₄ (20 g) was added. The mixture was stirred for 1 hour at 22° C., and filtered on a coarse fritted filter. The filtrate was concentrated under reduced pressure. No further purification was performed and the crude imine was used directly in the coupling reaction, Step 2, C.

2G. Preparation of

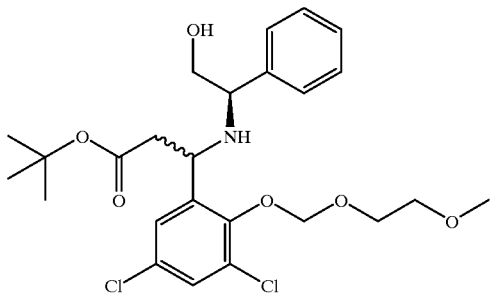

A 1-L 3-neck round bottom flask fitted with a mechanical stirrer and an addition funnel was charged with the solid reagent produced in Step 1 (91.3 g, 0.275 mol) and NMP (200 mL) under nitrogen. The solution was then cooled to −10° C. and stirred at 350 rpm. A solution of imine (prepared in Step 2B) in NMP was prepared under nitrogen and then added over 20 minutes to the above reaction mixture while the temperature was maintained at −5° C. (jacket temperature −10° C.). The mixture was stirred for an additional 1.5 hours at −8° C. and one hour at −5° C. after the addition was complete. After cooling to −10° C. a mixture of concentrated HCl/saturated solution of NH₄Cl (8.1 mL/200 mL) was added in 10 minutes. MTBE (200 ml) was added and the mixture was stirred 15 minutes at 23° C. at 200 rpm. Stirring was stopped and the layers separated. The aqueous layer was extracted with MTBE (100 mL). The two organic layers were combined, washed successively with a saturated solution of NH₄Cl (100 mL), water (100 mL) and brine (100 mL). The solution was dried with MgSO₄ (30 g), filtered and concentrated to afford an orange oil (66.3 g) (solidifies in standing) containing the desired product as a single diastereoisomer (confirmed by proton and carbon nmr). A sample was purified for analysis by recrystallization from heptane to afford the product as an off-white solid.

Proton and carbon NMR and IR spectra were consistent with the desired structure. $[\alpha]^D_{25}=+8.7°$ (c=1.057, MeOH). Microanalytical: calcd for $C_{25}H_{33}Cl_2NO_6$: C, 58.77%; H, 6.47%; N, 2.72%; Cl, 13.78% found: C, 58.22%; H, 6.54%; N, 2.70%; Cl, 13.66%.

Step 3

Preparation of

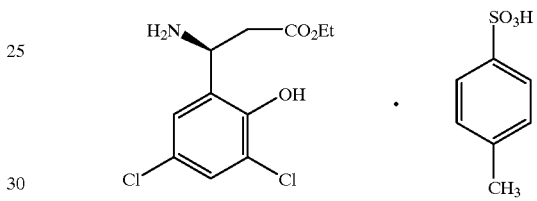

3A. A solution of the crude ester prepared in Step 2 [17.40 g, 0.033 mole (theory)], and EtOH (250 mL) was charged to a 1-L 3-neck jacketed reactor. The solution was cooled to 0° C. and Pb (OAc)₄ (14.63 g, 0.033 mole) was added at once. After 2 hours a 15% solution of NaOH (30 mL) was added and ethanol was removed under reduced pressure. Another portion of 15% NaOH (100 mL) was added and the mixture extracted with MTBE (2×100 mL), washed with H₂O (2×100 mL) and brine (50 mL), dried with Na₂SO₄, filtered on celite and concentrated under reduced pressure to afford an orange oil (12.46 g). The oil was homogeneous by thin layer chromatography (tic) and was used without further purification.

3B. The oil from 3A was diluted with EtOH (30 mL) and paratoluene sulfonic acid (1.3 equiv., 0.043 mole, 8.18 g) was added. The solution was heated to reflux for 8 hours, cooled to ambient temperature and concentrated under reduced pressure. The residue was treated with THF (20 mL) and heated to reflux to form a solution. The solution was cooled to room temperature and the compound crystallized. Heptane (30 mL) and THF (10 mL) were added to form a fluid slurry which was filtered. The cake was washed with THF/heptane (40 mL, 1/1) and vacuum dried for two hours in a pressure filter under nitrogen to afford a white solid (7.40 g).

Proton and carbon NMR and IR spectra were consistent with the desired product as substantially a single enantiomer. Microanalytical: calcd for $C_{18}H_{21}Cl_2NO_6S$, 0.25 $C_4H_8O$: C, 48.73%; H, 4.95%; N, 2.99%; Cl, 15.14% found: C, 48.91%; H, 4.95%; N, 2.90%; Cl, 14.95%.

Step 4
Preparation of

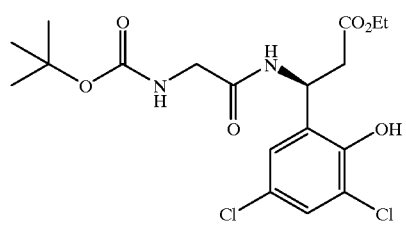

To a 500 mL round bottom flask equipped with a magnetic stir bar and nitrogen bubbler were charged the free base of the product produced in Step 3 (21.7 g, 0.065 mole), N-t-Boc-glycine N-hydroxysuccinimide ester (17.7 g, 0.065 mole) and DMF (200 mL). The reaction mixture was stirred under nitrogen at room temperature for 3.25 hours and a pale orange solution formed. The reaction mixture was poured into ice-cold ethyl acetate (1.2 L). The organic solution was washed with 1M HCl (250 mL) and then with brine (500 mL), dried (MgSO$_4$) and concentrated under vacuum to near dryness to obtain an oil that was subsequently dried at 50° C. to obtain the product as a colorless oil (28.12 g, 99%). Seed crystals were prepared from ethyl acetate/hexanes. The product (about 28 g) was dissolved in ethyl acetate (35 mL) and hexanes (125 mL). The solution was seeded with the seed crystals and precipitate formed. The solids were filtered and dried overnight under vacuum at 55° C. to yield a colorless solid (27.0 g, 95%).

MS and $^1$H NMR were consistent with the desired structure.

Step 5
Preparation of

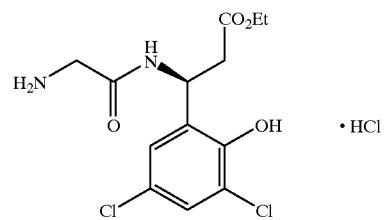

The Boc-protected glycine amide prepared in Step 4 (27.0 g, 0.062 mole) was dried overnight over P$_2$O$_5$ and NaOH pellets. The solid was dissolved in dioxane (40 mL) and the solution cooled to 0° C. An equivalent volume of 4N HCl/dioxane (0.062 mole) was added and the reaction was run for 2 hours. At this point the conversion was 80% by RPHPLC. The reaction mixture was allowed to warm to room temperature over 4 hours. The reaction mixture was concentrated at 40° C. to a foam which was triturated with ether (200 mL). The white solid that formed was filtered and dried over P$_2$O$_5$ to yield the desired glycine beta-amino acid ethyl ester compound, as an HCl salt (20.4 g, 88.5% isolated yield).

MS and $^1$H NMR were consistent with the desired structure.

EXAMPLE J
Preparation of

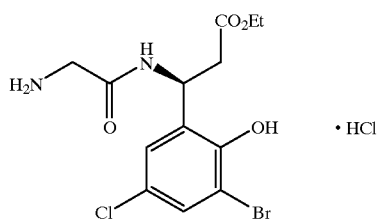

Step 1
Preparation of

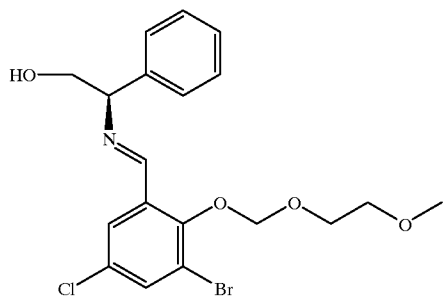

MEM protected 3-bromo-5-chlorosalicylaldehyde (129.42 g, 0.4 mol), prepared according to the procedure of Example I, Step 2A. An equivalent amount of 3-bromo-5-chlorosal icylaldehyde was substituted for 3,5-dichlorosalicylaldehyde, which was charged in a 2-L 3-neck round bottom flask fitted with a mechanical stirrer, followed by addition of THF (640 ml) and (S)-phenylglycinol (54.86 g, 0.4 mol). After 30 minutes at 22° C., MgSO$_4$ (80 g) was added. The mixture was stirred for 2 hours at 22° C., and filtered on a coarse fritted filter. The filtrate was concentrated under reduced pressure to afford a pale yellow oil (180.0 g) containing the desired imine. No further purification was performed and the crude product was used directly in the coupling reaction, Step 2. Microanalytical: calcd for C$_{19}$H$_{21}$BrClNO$_4$: C, 51.54%; H, 4.78%; N, 3.16%; Br, 18.04%; Cl, 8.00% found: C, 50.22%; H, 4.94%; N, 2.93%; Br, 17.15%; Cl, 7.56%.

Step 2
Preparation of

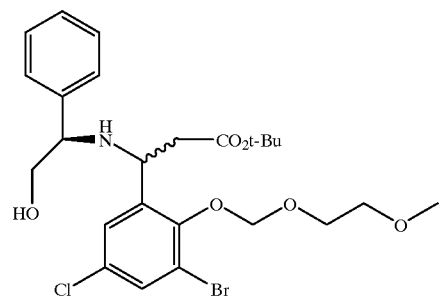

In a 5-L 3-neck round bottom flask fitted with a mechanical stirrer, the reagent from Example I, Step 1 (332.0 g, 0.8 mol) was taken up in NMP (660 mL) under nitrogen. The solution was then cooled to −10° C. A solution of imine from Step 1 in NMP (320 ml) was prepared under nitrogen and then added over 30 minutes to the above reaction mixture while the temperature was maintained at −5° C. The mixture was stirred for an additional hour at −8° C. and at −5° C. for 2 hours after addition was complete and then cooled to −10° C. A mixture of concentrated HCl/saturated solution of NH₄Cl (30 mL/720 mL) was added over 10 minutes. MTBE (760 ml) was added and the mixture was stirred for 30 minutes at 23° C. Stirring was stopped and the layers separated. The aqueous layer was extracted with MTBE (320 ml). The organic layers were combined, washed successively with saturated aqueous NH₄Cl (320 ml), DI water (320 ml) and brine (320 ml). The solution was dried with MgSO₄ (60 g), filtered and concentrated to afford a yellow oil (221.0 g) containing the desired product as a single diastereoisomer as determined by proton NMR. DSC: 211.80° C. (endo. 72.56 J/g), 228.34° C. (98.23 J/g); Microanalytical: calcd for C₂₅H₃₃BrClNO₆: C, 53.72%; H, 5.95%; N, 2.50%; Br, 14.29%; Cl, 6.33% found: C, 52.11%; H, 6.09%; N, 2.34%; Br, 12.84%; C, 6.33%.

Step 3

Preparation of

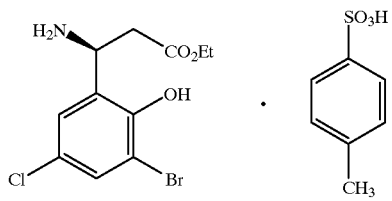

A solution of crude ester, prepared in Step 2 (~111 g), in ethanol (1500 mL) was charged under argon atmosphere to a 3-L 3-neck round bottom flask fitted with a mechanical stirrer. The reaction mixture was cooled to 0° C. and lead tetraacetate (88.67 g, 0.2 mol) was added in one portion. The reaction mixture was stirred for 3 hours at 0° C. and then 15% aqueous NaOH (150 mL) was added to the reaction mixture below 5° C. Methanol was removed under reduced pressure on rotavap. Another 150 mL of 15% aqueous NaOH was added and the reaction mixture was extracted with ethyl acetate (3×300 mL) and washed with DI water (2×100 mL) and brine (2×100 mL) and dried over anhydrous MgSO₄ (30 g). It was then filtered over celite and concentrated under reduced pressure to give the desired product (103 g) as a red oil.

Step 4

Preparation of

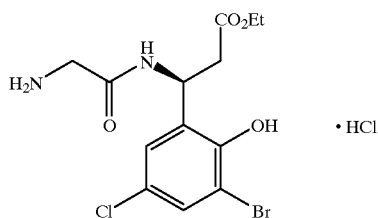

The above compound was prepared according to the procedure employed for Example I, Step 4 and Step 5 by substituting an equivalent amount of the product from Step 3 in Example I, Step 4. MS and ¹H NMR were consistent with the desired structure.

EXAMPLE K

Alternate Preparation of the Compound of Example J

Step 1

Preparation of

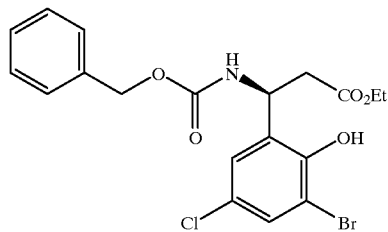

To the product of Example B, Step 3, (50.0 g, 139.2 mmol) and NaHCO₃ (33.5 g, 398.3 mmol) was added CH₂Cl₂ (500 mL) and water (335 mL). The mixture was stirred at room temperature for 10 minutes. A solution of benzyl chloroformate (38.0 g, 222.8 mmol) in CH₂Cl₂ (380 mL) was added over 20 minutes with rapid stirring. After 50 minutes, the reaction mixture was poured into a separatory funnel and the organic layer collected. The aqueous phase was washed with CH₂Cl₂ (170 mL). The combined organic layers were dried (MgSO₄) and concentrated in vacuo. The resulting gummy solid was triturated with hexane and collected by filtration. The tan solid was dried in vacuo to give the desired racemic product (61.2 g, 96% yield). This material was subjected to reverse phase HPLC using a chiral column to give each pure enantiomer. The column employed was a Whelk-O (R,R), 10 micron particle size using a 90:10 heptane:ethanol mobile phase. Optical purity was determined to be >98% using analytical hplc using similar column and solvent conditions. ¹H NMR was consistent with the proposed structure.

Step 2

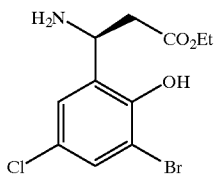

To a solution of the compound obtained in Step 1 (48.5 g, 106.2 mmol) in CH₂Cl₂ (450 mL) was added trimethylsilyl iodide (25.5 g, 127.4 mmol) in CH₂Cl₂ (100 mL) via canula. The orange solution was stirred at room temperature for 1 hour. Methanol (20.6 mL, 509.7 mmol) was added dropwise and the solution stirred for 15 minutes. The reaction solution was concentrated in vacuo to give an orange oil. The residue was dissolved in methyl t-butyl ether (500 mL) and extracted with 1 N HCl (318 mL) and water (1×200 mL, 1×100 mL). The aqueous extracts were back washed with MTBE (100 mL). To the aqueous solution was added solid NaHCO₃ (40.1 g, 478 mmol) in small portions. The basified aqueous mixture was extracted with MTBE (1×1 L, 2×200 mL). The combined organic solution was washed with brine and concentrated in vacuo to give the desired product (23.3 g, 68% yield). ¹H NMR was consistent with the proposed structure.

Step 3

Preparation of

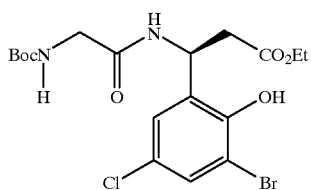

To a solution of the product from Step 2 (23.3 g, 72.1 mmol) in DMF (200 mL) was added N-t-Boc-glycine N-hydroxysuccinimide ester (17.9 g, 65.9 mmol). The reaction mixture was stirred at room temperature for 20 hours. The mixture was poured into ethyl acetate (1.2 L) and washed with 1M HCl (2×250 mL), saturated aqueous $NaHCO_3$ solution (2×250 mL) and brine (2×250 mL). The solution was dried ($MgSO_4$) and concentrated to give the desired product (32.0 g, 100% yield). Anal. calcd for $C_{18}H_{24}BrClN_2O_6$: C, 45.06; H, 5.04; N, 5.84. Found: C, 45.17; H, 5.14; N, 6.12.

$^1$H NMR was consistent with the desired structure.

Step 4

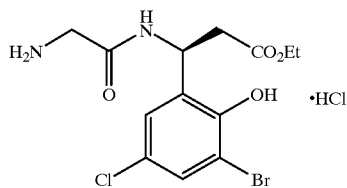

To a solution of the product of Step 3 (31.9 g, 66.5 mmol), in absolute ethanol (205 mL) was added an ethanolic HCl solution (111 mL of a 3M solution, 332.4 mmol). The reaction solution was heated at 58° C. for 30 minutes. The solution was cooled and concentrated in vacuo. The residue was dissolved in ethyl acetate (250 mL) and stirred at 0° C. for 2 hours. A white precipitate was collected by filtration and washed with cold ethyl acetate. The solid was dried in vacuo to give the desired product (23.5 g, 85% yield). Anal. calcd for $C_{13}H_{16}BrClN_2O_4$+1.0 HCl: C, 37.53; H, 4.12; N, 6.73. Found: C, 37.29; H, 4.06; N, 6.68.

$^1$H NMR was consistent with the desired structure.

EXAMPLE L

Preparation of

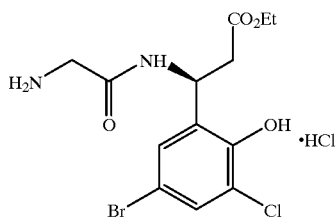

Step 1

Preparation of

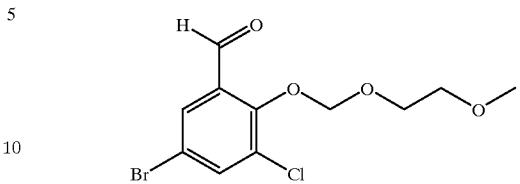

Potassium carbonate (powder, oven dried at 100° C. under vacuum, 22.1 g, 0.16 moles) was added to a solution of 3-chloro-5-bromosalicylaldehyde (35.0 g, 0.15 moles) in DMF (175 ml) at room temperature to give a bright yellow slurry. MEMCl (neat, 25.0 g, 0.2 moles) was then added while maintaining the bath temperature at 20° C. The mixture was then stirred at 22° C. for 6 hours and was poured into DI water (1200 mL) to precipitate the product. The slurry was filtered on a pressure filter and the cake was washed with DI water (2×400 mL) and was dried under $N_2$/vacuum to afford the product (46.0 g, 95% yield) as an off white solid. $^1$H NMR ($CDCl_3$, TMS) 3.35 (s, 3H), 3.54 to 3.56 (m, 2H), 3.91 to 3.93 (m, 2H), 5.30 (s, 2H), 7.77 (d, 1H), 7.85 (d, 1H), 10.30 (s, 1H); $^{13}$C NMR ($CDCl_3$, TMS) (ppm):59.05, 70.11, 71.49, 99.50, 117.93, 129.69, 129.78, 132.37, 138.14, 155.12, 188.22. DSC: 48.24° C. (endo 90.51 J/g); Microanalytical: calcd for $C_{11}H_{12}BrClO_4$: C, 40.82%; H, 3.74%; Cl, 10.95%; Br, 24.69%; found: C, 40.64%; H, 3.48%; Cl, 10.99%; Br, 24.67%.

Step 2

Preparation of

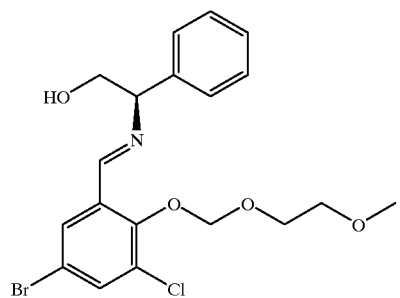

The product from Step 1 (32.35 g., 0.1 mol) was charged in a 500 ml 3N round bottom flask fitted with a mechanical stirrer, followed by addition of THF (160 ml) and (S)-phenylglycinol (13.71 g, 0.1 mol). After 30 minutes at 22° C., $MgSO_4$ (20 g.) was added. The mixture was stirred for 1 hour at 22° C. and filtered on a coarse fritted filter. The filtrate was concentrated under reduce pressure to afford a pale yellow oil (48.0 g) containing the desired imine. No further purification was performed and the crude product was used directly in the next reaction step. Microanalytical: calcd for $C_{19}H_{21}BrClNO_4$: C, 51.54%; H, 4.78%; N, 3.16%; Br, 18.04%; Cl, 8.00% found: C, 51.52%; H, 5.02%; N, 2.82%; Br, 16.31%; Cl, 7.61%.

Step 3
Preparation of

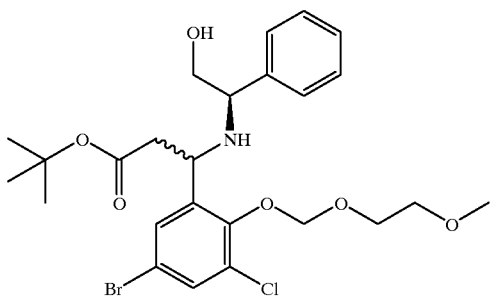

In a 5 L 3N round bottom flask fitted with a mechanical stirrer, reagent from Example I, Step 1, (332 g, 0.8 mol) was taken up in NMP (660 mL) under nitrogen. The solution was then cooled to −10° C. A solution of imine produced in Step 2, in NMP (320 ml) was prepared under nitrogen and then added over 30 minutes to the above reaction mixture while the temperature was maintained at −5° C. The mixture was stirred for an additional hour after the addition was complete and cooled to −10° C. A mixture of concentrated HCl/saturated solution of NH$_4$Cl (30 mL/720 mL) was added over 10 minutes. MTBE (760 ml) was added and the mixture was stirred for 1 hour at 23° C. Stirring was stopped and the layers were separated. The aqueous layer was extracted with MTBE (320 ml). The two organic layers were combined, washed successively with a saturated solution of NH$_4$Cl (320 ml), DI water (320 ml) and brine (320 ml). The solution was dried with MgSO$_4$ (60 g), filtered and concentrated to afford a yellow oil (228 g) containing the desired product as a single diastereoisomer. DSC: 227.54° C. (endo. 61.63 J/g); Microanalytical: calcd for C$_{25}$H$_{33}$BrClNO$_6$: C, 53.72%; H, 5.95%; N, 2.50%; Br, 14.29%; Cl, 6.33% found: C, 53.80%; H, 6.45%; N, 2.23%; Br, 12.85%; Cl, 6.12%.

Step 4
Preparation of

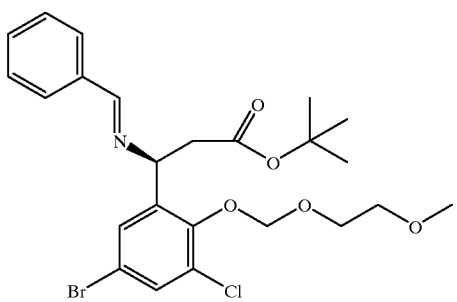

A solution of crude ester produced in Step 3 (~111 g) in ethanol (1500 mL) was charged under nitrogen atmosphere to a 3 L 3N round bottom flask fitted with a mechanical stirrer. The reaction mixture was cooled to 0° C. and lead tetraacetate (88.67 g, 0.2 mol) was added in one portion. The reaction mixture was stirred for 3 hours at 0° C. and then 15% aqueous NaOH (150 mL) was added to the reaction mixture below 5° C. The ethanol was removed under reduced pressure on rotavap. Another 600 mL of 15% aqueous NaOH was added and the reaction mixture was extracted with ethyl acetate (2×300 mL), MTBE (2×200 mL) and ethyl acetate (2×200 mL). The organic layers were combined and washed with DI water (2×200 mL) and brine (2×100 mL) and dried over anhydrous MgSO$_4$ (30 g). The solution was then filtered over celite and concentrated under reduced pressure to give the product as an orange oil (96 g) that was used in the next step without further purification. DSC: 233.60° C. (endo. 67.85 J/g); Microanalytical: calcd for C$_{24}$H$_{29}$BrClNO$_5$: C, 54.71%; H, 5.54%; N, 2.65%; Br, 15.16%; Cl, 6.72% found: C, 52.12%; H, 5.40%; N, 2.47%; Br, 14.77%; Cl, 6.48%.

Step 5
Preparation of

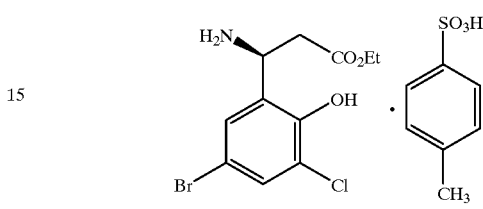

The crude product from Step 4 (~94 g) was taken up in absolute ethanol (180 mL) and para toluenesulfonic acid monohydrate (50.0 g, 0.26 mol) was added. The reaction mixture was then heated to reflux for 8 hours after which the solvent was removed under reduced pressure. The residual solid was taken up in THF (100 mL) and the THF was then stripped off under reduced pressure. The residue was dissolved in ethyl acetate (500 mL) and cooled to −5° C. The solid was filtered and washed with heptane (2×50 mL) to give a white solid. The solid was then air dried to give the desired product as a white solid (38 g) as a single isomer. $^1$H NMR (DMSO, TMS) (ppm) 1.12 (t, 3H), 2.29 (s, 3H), 3.0 (m, 2H), 4.05 (q, 2H), 4.88 (t, 1H), 7.11 (d, 2H), 7.48 (d, 2H), 7.55 (d, 1H), 7.68 (1H, d), 8.35 (br. s, 3H); $^{13}$C NMR (DMSO, TMS) (ppm):13.82, 20.75, 37.13, 45.59, 60.59, 110.63, 122.47, 125.44, 127.87, 128.06, 129.51, 131.95, 137.77, 145.33, 150.14, 168.98; DSC:69.86° C. (end., 406.5 J/g), 165.72° C. (end. 62.27 J/g), 211.24° C. (exo. 20.56 J/g) $[\alpha]^D_{25}$=+4.2° (c=0.960,MeOH); IR (MIR) (cm-1)2922, 1726, 1621, 1591, 1494, 1471, 1413, 1376, 1324, 1286, 1237, 1207;. Microanalytical: calcd for C$_{18}$H$_{21}$BrClNO$_6$S: C, 43.69%; H, 4.27%; N, 2.83%; Br, 16.15%; Cl, 7.16%; S, 6.48% found: C, 43.40%; H, 4.24%; N, 2.73%; Br, 16.40%; Cl, 7.20%, S, 6.54%.

Step 6
Preparation of

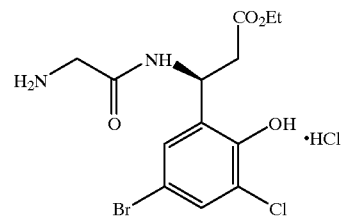

The above compound was prepared according to the procedures outlined in Example I, Step 4 and Step 5 where an equivalent quantity of the intermediate prepared in Step 5 as the free base is substituted fin Example I, Step 4.

MS and $^1$H NMR were consistent with the desired structure.

EXAMPLE M

Preparation of

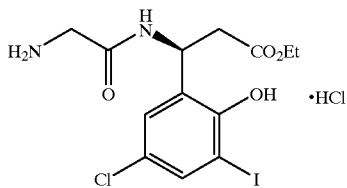

Step 1

Preparation of 3-Iodo-5-chlorosalicylaldehyde

N-Iodosuccinimide (144.0 g, 0.641 mole) was added to a solution of 5-chlorosalicylaldehyde (100 g, 0.638 mole) in dimethylformamide (400 mL). The reaction mixture was stirred for 2 days at room temperature. Additional N-iodosuccinimide (20.0 g) was added and stirring was continued for additional 2 days. The reaction mixture was diluted with ethyl acetate (1 L), washed with hydrochloric acid (300 mL, 0.1N), water (300 mL), sodium thiosulfate (5%, 300 mL), brine (300 mL), dried ($MgSO_4$) and was concentrated to dryness to afford the desired aldehyde as a pale yellow solid (162 g, 90% yield).

MS and $^1$H NMR were consistent with the desired structure.

Step 2

Preparation of 2-O-(MEM)-3-iodo-5-chlorosalicylaldehyde

Potassium carbonate (41.4 g, 0.30 mole) was added to a solution of 3-iodo-5-chlorosalicylaldehyde (84.74 g, 0.30 mole) in DMF (200 mL) at 20° C. This resulted in a yellow slurry and MEM-Cl (38.2 g, 0.305 mole) was added maintaining the reaction temperature. After 2 hours, additional MEM-Cl (1.5 g) was added. After stirring for 1 hour, the reaction mixture was poured into an ice-water mixture and was stirred. The precipitate formed, was filtered, and was dried in vacuo to afford the desired protected aldehyde. Yield: 95 g (85%).

MS and $^1$H NMR were consistent with the desired structure.

Step 3

Preparation of

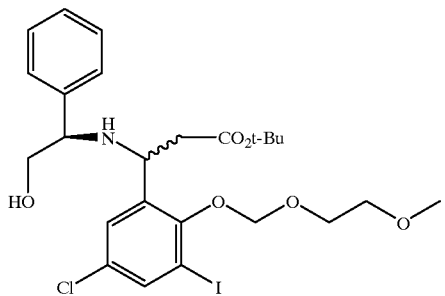

(S)-Phenyl glycinol (15.37 g, 0.112 mole) was added to a solution of 2-O-(MEM)-3-iodo-5-chlorosalicylaldehyde (41.5 g, 0.112 mole) in THF (200 mL) at room temperature. After 1 hour of stirring $MgSO_4$ (16 g) was added and the stirring was continued for 2 hours. The reaction mixture was filtered and the filtrate was concentrated and was dried in vacuo for 2 hours to obtain the desired intermediate imine.

A 2-neck round bottomed flask was charged with the Reformatsky reagent from Example I, Step 1, (81.8 g, 0.2464 mole) and N-methylpyrrolidone (300 mL) and was stirred at −10° C. A solution of the imine in N-methylpyrrolidone (100 mL) was slowly added maintaining the temperature at −10° C. The mixture was maintained at this temperature for 2 hours and for 1 hour at −5° C. After cooling the reaction mixture to −10° C., a solution of concentrated HCl in saturated ammonium chloride (16 ml/200 mL) was added. Ethyl ether (500 mL) was added and was stirred for 2 hours at room temperature. The ether layer was separated, and the aqueous layer was further extracted with ether (300 mL). The combined ether layers were washed with saturated ammonium chloride (200 mL), water (200 mL), brine (200 mL), dried ($MgSO_4$) and concentrated to afford an oil (61.0 g, 90% yield). $^1$H NMR indicated that the desired structure was substantially one diastereomer and MS was consistent with the desired structure.

Step 4

Preparation of

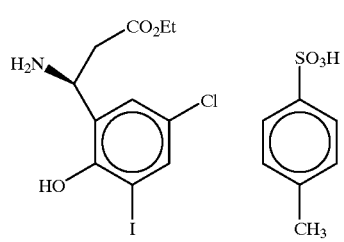

A solution of the crude ester produced in Step 3 (48.85 g, 80.61 mmol) was dissolved in ethanol (500 mL) and was cooled to 0° C. Lead tetraacetate (35.71 g, 80.61 mmol) was added. After 3 hours, 15% solution of NaOH (73 mL) was added to the reaction mixture. Most of the ethanol was removed under reduced pressure. To the residue was added a 15% solution of NaOH (200 mL) and which was then extracted with ether (400 mL). The ether layer was washed with water (100 mL), brine (100 mL), dried and was concentrated to afford an orange oil. The oil was dissolved in ethanol (100 mL) and para-toluenesulfonic acid (19.9 g) was added. The solution was heated at reflux for 8 hours and was concentrated under reduced pressure. The residue was diluted with THF (60 mL) and was heated at reflux and was cooled. The precipitate was filtered, washed with hexane/THF (300 mL, 1:1) and dried to afford the desired product.

MS and $^1$H NMR were consistent with the desired structure.

Step 5

S-Ethyl 3-(N-BOC-gly)-amino-3-(S)-(5-chloro-2-hydroxy-3-iodo)phenyl propionate To a mixture of BOC-gly-OSu (9.4 g, 34.51 mmol), ethyl 3-(S)-amino-3-(5-chloro-2-hydroxy-3-iodo) propionate PTSA salt (17.0 g, 31.38 mmol) in DMF (200 mL) was added triethylamine (4.8 mL). The reaction mixture was stirred for 18 hours at room temperature. The DMF was removed in vacuo and the residue was partitioned between ethyl acetate (600 mL) and diluted hydrochloric acid (100 mL). The organic layer was washed with sodium bicarbonate (200 mL), brine (200 mL), dried ($MgSO_4$) and was concentrated to afford of the desired product as a solid (14.2 g, 86% yield).

MS and $^1$H NMR were consistent with the desired structure.

Step 6

S-Ethyl 3-(N-gly)-amino-3-(5-chloro-2-hydroxy-3-iodo)phenyl propionate hydrochloride Dioxane/HCl (4N, 70 mL) was added to ethyl 3-(S)-(N-BOC-gly)-amino-3-(5-chloro-2-hydroxy-3-iodo)phenyl propionate (37.20 g, 70.62 mmol) at 0° C. and was stirred at room temperature for 3 hours. The reaction mixture was concentrated, and concentrated once more after addition of toluene (100 mL). The residue obtained was suspended in ether, was filtered and dried to afford the desired product as a crystalline powder (32.0 g, 98% yield).

MS and $^1$H NMR were consistent with the desired structure.

EXAMPLE N

Preparation of

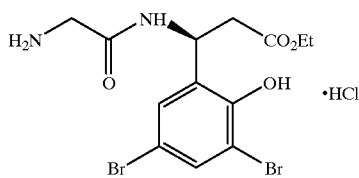

Step 1
Preparation of

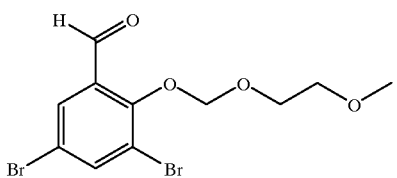

The above compound was prepared according to Example I, Step 2A, substituting an equivalent quantity of 2-hydroxy-3,5-dibromobenzaldehyde for 3,5-dichlorosalicylaldehyde. Yield 88%; Pale yellow solid; m. p. 46–47° C.; $R_f$=0.6 (EtOAc/Hexane 1:1 v/v); $^1$H-NMR (CDCl$_3$) d 3.37 (s, 3H), 3.56 (m, 2H), 3.92 (m, 2H), 5.29 (s, 2H), 7.91 (d, 1H, J=2.4 Hz), 7.94 (d, 1H, J=2.4 Hz), 10.27 (s, 1H); FAB-MS m/z 367 (M$^+$) HR-MS calculated for C$_{11}$H$_{12}$Br$_2$O$_4$ 367.9083 found 367.9077.

MS and $^1$H NMR were consistent with the desired structure.

Step 2

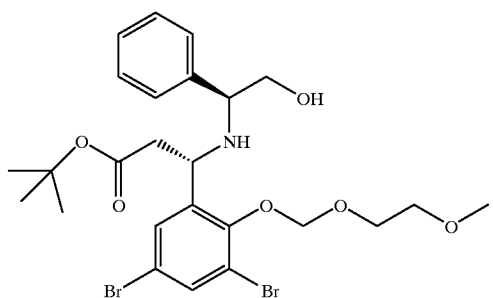

The above compound was prepared using the procedure of Example I, Step 2B and Step 2C, substituting an equivalent quantity of the compound of Step 1 in Example I, Step 2B. Yield 90%; Yellow solid; m. p. 57–59° C.; $R_f$=0.46 (EtOAc/Hexane 1:1 v/v); $^1$H-NMR (CDCl$_3$) d 1.45 (s, 9H); 2.1 (br, 1H, exchangeable), 2.51 (d, 1H, J$_1$=9.9 Hz, J$_2$=15.3 Hz), 2.66 (d, 1H, J$_1$=4.2 Hz, J$_2$=15.3 Hz), 3.02 (br, 1H, exchangeable), 3.39 (s, 3H), 3.58–3.62 (m, 4H), 3.81 (m, 1 H), 3.93 (m, 2H), 4.63 (dd, 1H, J=4.2 Hz), 5.15 (s, 2H), 7.17–7.25 (m, 6H), 7.49 (d, 1H); FABMS m/z 602 (M+H)

HR-MS calculated for C$_{25}$H$_{34}$NBr$_2$O$_6$ 602.0753 found 602.0749.

MS and $^1$H NMR were consistent with the desired structure.

Step 3

Preparation of

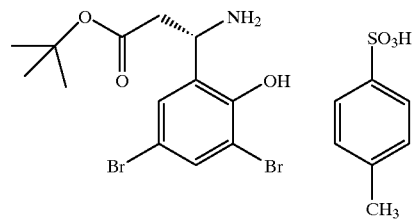

The above compound (p-toluenesulfonate salt) was prepared according to Example I, Step 3 by substituting an equivalent quantity of the product prepared in Step 2 in Example I, Step 3A. Yield 62%; white solid; $^1$H-NMR (DMSO-d$_6$) d 1.09 (t, 3H, J=7.2 Hz), 2.27 (s, 3H), 2.97(dd, 2H, J$_1$=3.0 Hz, J$_2$=7.2 Hz), 4.02 (q, 2H, J=7.2 Hz), 4.87 (t, 1 H, J=7.2 Hz), 7.08 (d, 2H, J=4.8 Hz), 7.45 (m, 3H), 7.57 (d, 1H, J=2.4 Hz), 8.2 (br,3H); FABMS m/z 365 (M+H)

HR-MS calculated for C$_{11}$H$_{14}$NBr$_2$O$_3$, 365.9340 found 365.9311.

MS and $^1$H NMR were consistent with the desired structure.

Step 4

Preparation of

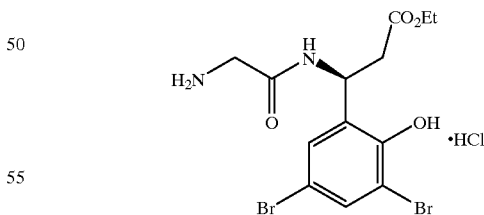

The above compound was prepared using the procedure of Example I, Step 4 substituting the compound prepared in Step 3. The resulting BOC protected intermediate, was converted to the desired compound using the procedure of Example I, Step 5.

MS and $^1$H NMR were consistent with the desired structure.

EXAMPLE P

Preparation of

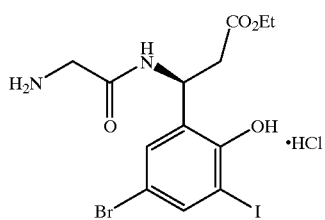

The above compound is prepared according to the procedure of Example I by substituting an equivalent amount of 3-iodo-5-bromosalicylaldehyde prepared in Example F, Step 1 for 3,5-dichlorosalicylaldehyde in Example I, Step 2 A.

EXAMPLE 1

(±) 3-bromo-5-chloro-2-hydroxy-β-[[2-[[[3-hydroxy-5-[(1,4,5,6-tetrahydro-5-hydroxypyrimidin-2-yl)amino]phenyl]carbonyl]amino]-acetyl]amino] benzenepropanoic acid, trifluroacetate salt Preparation of

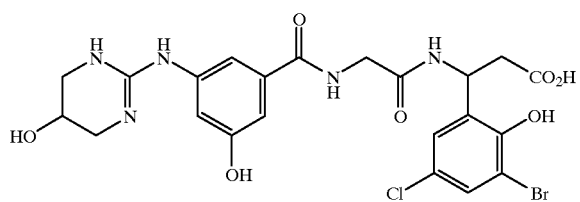

To the product of Example H (0.4 g, 0.0014 mole), the product of Example B (0.58 g, 0.0014 mole), triethylamine (0.142 g, 0.0014 mole), DMAP (17 mg), and anhydrous DMA (4 ml) was added EDCl (0.268 g, 0.0014 mole) at ice bath temperature. The reaction was stirred overnight at room temperature. The resulting ester intermediate was isolated by reverse phase preparatory HPLC. To this ester in $H_2O$ (10 ml) and $CH_3CN$ (5 ml) was added LiOH (580 mg, 0.0138 mole). After stirring at room temperature for 1 hour, the pH was lowered to 2 with TFA and the product was purified by reverse phase preparatory HPLC to yield (after lyophilization) the desired product as a white solid (230 mg).

MS and $^1$H NMR were consistent with the desired structure.

EXAMPLE 2

Preparation of

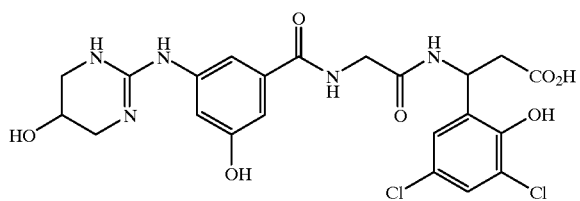

The above compound was prepared according to the methodology of Example 1, substituting an equivalent amount of the product from Example A for the product from Example B. The yield, after lyophilization was 320 mg of as a white solid.

MS and $^1$H NMR were consistent with the desired structure.

EXAMPLE 3

Preparation of

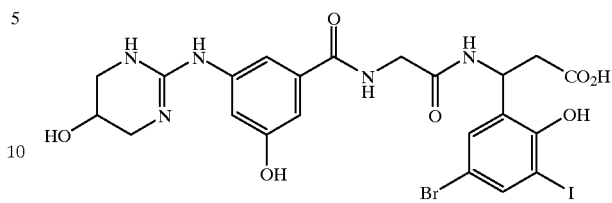

The above compound was prepared according to the methodology of Example 1, substituting an equivalent amount of the product from Example F for the product from Example B. The yield (after lyophilization) was 180 mg as a white solid.

MS and $^1$H NMR were consistent with the desired structure.

EXAMPLE 4

Preparation of

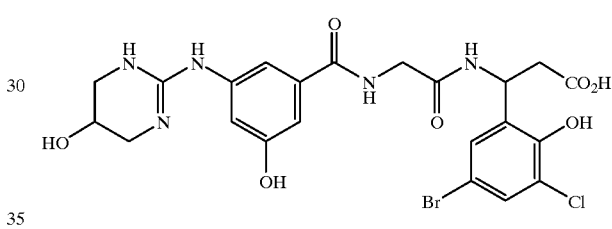

The above compound was prepared according to the methodology of Example 1, substituting an equivalent amount of the product of Example D for the product of Example B. The yield (after lyophilization) was 180 mg as a white solid.

MS and $^1$H NMR were consistent with the desired structure.

EXAMPLE 5

Preparation of

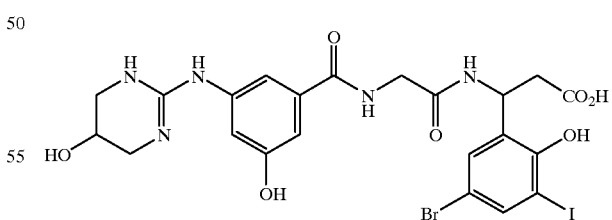

The above compound was prepared according to the methodology of Example 1, substituting an equivalent amount of the product from Example E for the product from Example B. The yield (after lyophilization) was 250 mg as a white solid.

MS and $^1$H NMR were consistent with the desired structure.

EXAMPLE 6

Preparation of

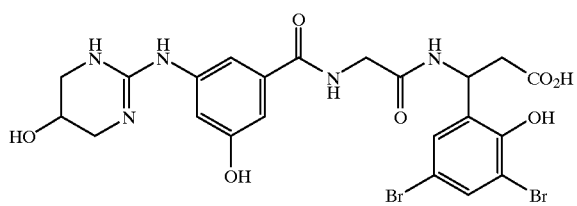

The above compound was prepared according to the methodology of Example 1, substituting an equivalent amount of the product from Example C for the product from Example B. The yield (after lyophilization) was 220 mg as a white solid.

MS and $^1$H NMR were consistent with the desired product.

EXAMPLE 7

Preparation of

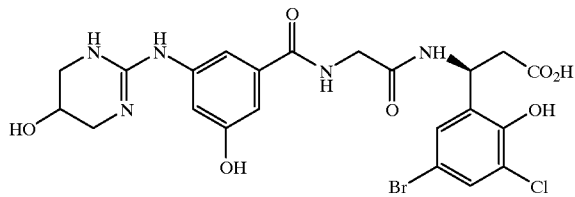

To the product from Example H (7.8 g, 0.027 mole) dissolved in anhydrous DMA (50 mL) in a flame dried flask under $N_2$ and at ice bath temperature was slowly added isobutylchloroformate (3.7 g, 0.027 mole) followed by N-methylmorpholine (2.73 g, 0.027 mole). The solution was stirred at ice bath temperature for 15 minutes. To the reaction mixture was then added the product from Example L (10.0 g, 0.024 mole) at ice bath temperature followed by N-methylmorpholine (2.43 g, 0.024 mole). The reaction was then stirred at room temperature overnight. The resulting ester intermediate was isolated by reverse phase prep HPLC. To the ester in $H_2O$ (60 mL) and $CH_3CN$ (30 mL) was added LiOH (10 g, 0.238 mole). The reaction mixture was stirred at room temperature for 1 hour. The pH was then lowered to 2 with TFA. The product was purified by reverse phase prep HPLC to yield (after lyophilization) the desired product as a white solid (9.7 g).

MS and $^1$H NMR were consistent with the desired structure.

EXAMPLE 8

(S) 3,5-dichloro-2-hydroxy-β-[[2-[[[3-hydroxy-5-[(1,4,5,6-tetrahydro-5-hydroxypyrimidin-2-yl)amino]phenyl]carbonyl]amino]acetyl]amino]-benzenepropanoic acid, monohydrochloride monohydrate Preparation of

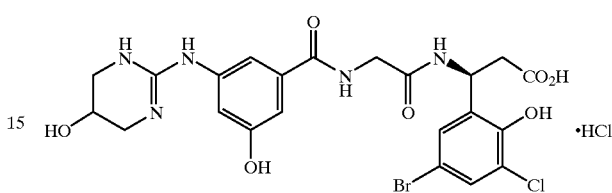

Step A

To the product from Example H (9.92 g, 0.0345 mole) dissolved in anhydrous DME (200 mL) is added N-methylmorpholine (4.0 mL, 0.0362 mole). The reaction mixture was cooled to −5° C. (salt-ice bath). Isobutylchloroformate, IBCF (4.48 mL, 4.713 g, 0.0345 mole) was added over one minute and the reaction mixture stirred at ice bath temperature for 12 minutes. To the reaction mixture was then added the product from Example I (11.15 g, 0.030 mole) at ice bath temperature followed by N-methylmorpholine (4.0 mL, 0.0362 mole). The reaction mixture was allowed to warm to room temperature and go to completion then concentrated under vacuum at 50° C. to give a dark residue. The residue was dissolved in acetonitrile: $H_2O$ (about 50 mL). The pH was made acidic by addition of a small amount of TFA. The residue was placed on a 10×500 cm C-18 (50 u particle size) column and the ester of the desired product isolated. (Solvent program: 100% $H_2O$+0.05% TFA to 30:70 $H_2O$+0.05% TFA:acetonitrile+0.05% TFA over 1 hour @ 100 mL/minute: the solvent program was initiated after the solvent front elutes). Preparatory RPHPLC purification resulted in a white solid (10.5 g) after lyophilization (50%).

MS and $^1$H NMR were consistent with the desired structure.

Step B

The product produced in Step A (about 11 g) was dissolved in dioxane:water and the pH of the solution adjusted to approximately 11.5 (pH meter) by the addition of 2.5 N NaOH. The reaction mixture was stirred at room temperature. Periodically, the pH was re-adjusted to >11 by further addition of base. After 2–3 hours the conversion of ester to acid was deemed complete by RPHPLC. The pH of the reaction mixture was adjusted to about 6 and a viscous oil precipitated from solution. The oil was isolated by decantation and washed with hot water (200 mL). The resulting aqueous mixture was allowed to cool and the solid was collected by filtration to yield The above compound (2.6 g after lyophilization from HCl solution). The residue, which was a dark viscous oil was treated with hot water to give on cooling a tan powder (4.12 g after lyophilization from HCl solution).

MS and $^1$H NMR were consistent with the desired structure.

EXAMPLE 9

(S) 3-bromo-5-chloro-2-hydroxy-β-[[2-[[[3-hydroxy-5-[(1,4,5,6-tetrahydro-5-hydroxypyrimidin-2-yl)amino]phenyl]carbonyl]amino]acetyl]amino]-benzenepropanoic acid, trifluoroacetate salt Step 1

Preparation of

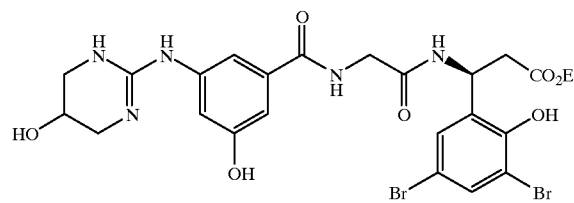

To a suspension of the product from Example J (1.0 g, 2.4 mmol), the product from Example H (0.75 g, 2.6 mmol) and 4-dimethylaminopyridine (40 mg) in N,N-dimethylacetamide (10 mL) was added triethylamine (0.24 g, 2.4 mmol). The mixture was stirred at room temperature for 15 minutes and 1-(3-dimethylaminopropyl)-3-ethylcarbodiimide hydrochloride (0.60 g, 3.1 mmol). The reaction mixture was stirred at room temperature overnight. The mixture was concentrated in vacuo and purified by reverse phase HPLC (starting gradient 90:10 $H_2O$/TFA:MeCN, retention time 22 minutes) to give the desired product, (1.6 g, 52% yield).

$^1H$ NMR was consistent with the proposed structure.

Step 2

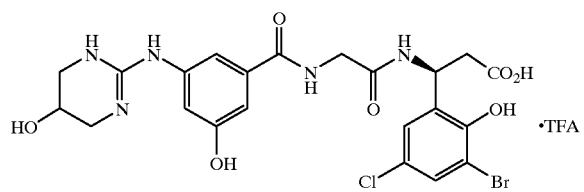

To a solution of the ester produced in Step 1 (800 mg, 1.2 mmol) in a 1:4 MeCN:$H_2O$ solution (7 mL) was added lithium hydroxide (148 mg, 6.2 mmol). The reaction mixture was stirred at room temperature for 2 hours. TFA (0.71 mL, 9.2 mmol) was added and the mixture purified by reverse phase HPLC (starting gradient 95:5 $H_2O$/TFA:MeCN, retention time 24 minutes) to give the desired product (860 mg, 83% yield). Anal. calcd for $C_{22}H_{23}BrClN_5O_7$+1.7 TFA: C, 39.18; H, 3.20; N, 8.99. Found: C, 39.11; H, 3.17; N, 9.07.

MS and $^1H$ NMR were consistent with the desired structure.

Step 3

Preparation of the hydrochloride salt

The product of Step 2 was dissolved in a suitable solvent (acetontrile water) and the solution slowly passed through a Bio-Rad AG2-8X (chloride form, 200–400 mesh, >5 equivalents) ion-exchange column. Lyophilization gives the desired product as an HCl salt.

EXAMPLE 10

Preparation of

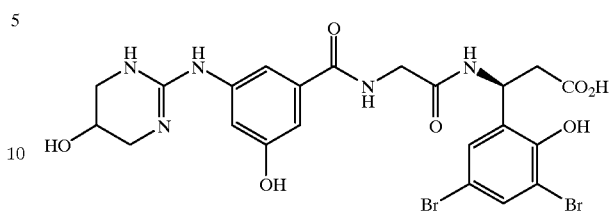

The above compound was prepared using the procedure of Example 8 substituting the product of Example N for the product of Example I in Example 8, Step A. The product was isolated by prep RPHPLC and lyophilized to give the desired product as a TFA salt.

MS and $^1H$ NMR were consistent with the desired structure.

EXAMPLE 11

Preparation of

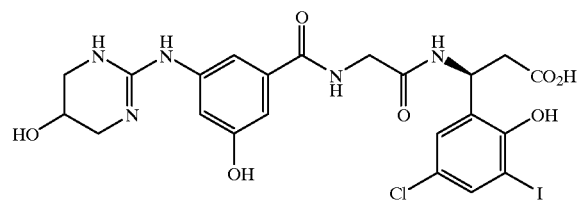

The above compound was prepared using essentially the procedures of Example 8 and substituting the product of Example M for the product of Example I in Example 8, Step A. The product was isolated by preparatory RPHPLC and lyophilized to give the desired product as a TFA salt.

MS and $^1H$ NMR were consistent with the desired structure.

EXAMPLE 12

Preparation of

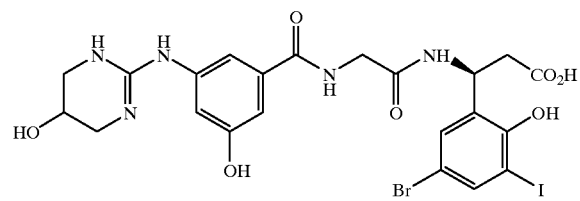

The above compound was prepared using the procedures of Example 8 and substituting the product of Example P for the product of Example I in Example 8, Step A. The product is isolated by prep RPHPLC and lyophilized to give the desired product as a TFA salt.

EXAMPLE 13

Preparation of

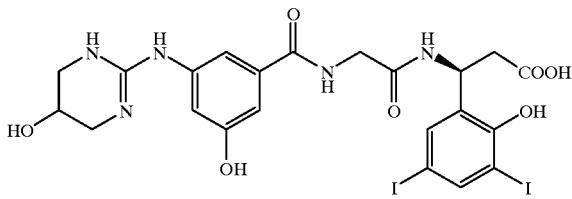

Preparation of 2-O-(MEM)-3,5-diiodosalicylaldehyde

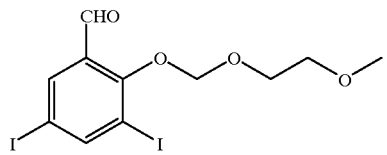

Potassium carbonate (18.5 g, 0.134 mole) was added to a solution of 3,5-diiodosalicylaldehyde (50.0 g, 0.134 mole) in DMF (150 mL) at 20° C. This resulted in a yellow slurry and MEM-CI (15.8 mL, 0.134 mole) was added maintaining the reaction temperature. After 2 hours, additional MEM-Cl (1.5 g) was added. After stirring for a further 1 hour, the reaction mixture was poured into ice-water and stirred. The precipitate formed, was filtered, and dried in vacuo to afford the desired protected aldehyde (61 g, 99% yield). $^1$H NMR was consistent with the desired product.

Step 2

Preparation of

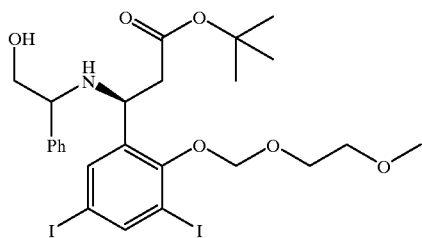

(S)-phenyl glycinol (17.9 g, 0.13 mole) was added to a solution of 2-O-(MEM)-3,5-diiodosalicylaldehyde (41.5 g, 0.112 mole) in THF (150 mL) at room temperature. After 1 hour of stirring MgSO$_4$ (20.7 g) was added and the stirring was continued for 2 hours. The reaction mixture was filtered and the filtrate was concentrated and dried in vacuo for 2 hours. A 2-neck round bottomed flask was charged with the Reformatsky reagent (96 g, 0.289 mole) and N-methylpyrrolidone (250 mL) and was stirred at −10° C. A solution of the imine in N-methylpyrrolidone (100 mL) was slowly added maintaining the temperature at −10° C. The mixture was maintained at this temperature for 2 hours and for 1 hour at −5° C. After cooling the reaction mixture to −10°C., a solution of concentrated HCl in saturated ammonium chloride (16 ml/200 mL) was added. Ethyl ether (500 mL) was added and the mixture was stirred for 2 hours at room temperature. The ether layer was separated, and the aqueous layer further extracted with ether (300 mL). The combined ether layers were washed with saturated ammonium chloride (200 mL), water (200 mL), brine (200 mL), dried (MgSO$_4$) and concentrated to afford an oil (90.0 g, 99% yield). NMR indicated desired product and one diastereomer.

Step 3

Preparation of

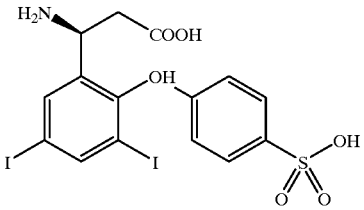

A solution of the crude ester from Step 2 (14.0 g, 20.1 mmol) was dissolved in ethanol (100 mL) and was cooled to 0° C. Lead tetra acetate (9.20 g, 20.75 mmol) was added in one lot. After 3 hours, 15% solution of NaOH (73 mL) was added to the reaction mixture. Most of the ethanol was removed under reduced pressure. The residue was added to a 15% solution of NaOH (200 mL) which was extracted with ether (400 mL). The ether layer was washed with water (100 mL), brine (100 mL), dried and concentrated to afford an orange oil. This was dissolved in ethanol (100 mL) and para-toluenesulfonic acid (6.08 g) was added. The solution was heated at reflux for 8 hours and was concentrated under reduced pressure. The residue was diluted with THF (60 mL), was heated at reflux and was cooled. Upon storage, no precipitate formed. The reaction mixture was concentrated and purified by preparative hplc to afford the amino acid as its PTSA salt. The solid obtained was dissolved in ethanol and was saturated with HCl gas. The reaction mixture was heated at reflux for 6 hours. The reaction mixture was concentrated to afford the PTSA salt of the desired amino acid (12.47 g).

Step 4

Preparation of Ethyl 3-(N-BOC-gly)-amino-3-(S)-(3,5-diiodo-2-hydroxyphenyl)propionate

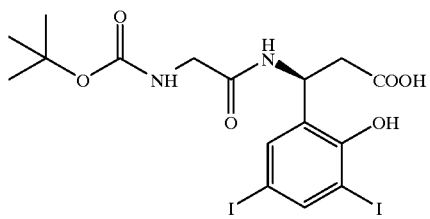

To a mixture of BOC-gly-OSu (7.48 g, 27.04 mmol), ethyl 3-(S)-amino-3-(3,5-diiodo-2-hydroxyphenyl)propionate PTSA salt (12.47 g, 27.04 mmol) in DMF (100 mL) was added triethylamine (3.8 mL). The reaction mixture was stirred for 18 hours at room temperature. The DMF was removed in vacuo and the residue partitioned between ethyl acetate (600 mL) and dilute hydrochloric acid (100 mL). The organic layer was washed with sodium bicarbonate (200 mL), brine (200 mL), dried (MgSO4) and concentrated to afford the desired product as a solid (17.0 g, 96% yield). $^1$H NMR was consistent with the desired product.

Step 5

Preparation of ethyl 3-(N-gly)-amino-3-(3,5-diiodo-2-hydroxyphenyl)propionate hydrochloride

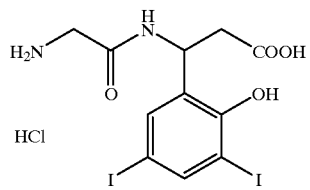

To dioxane/HCl (4N, 40 mL) was added ethyl 3-(N-BOC-gly)-amino-3-(S)-(3,5-diiodo-2-hydroxyphenyl)propionate (17.0 g, 25.97 mmol) at 0° C. and the reaction mixture was stirred at room temperature for 3 hours. The reaction mixture was concentrated, and concentrated once more after addition of toluene (100 mL). The residue obtained was dried to afford the desired product as a crystalline powder (8.0 g, 56% yield). $^1$H NMR is consistent with the desired product.

Step 6

A solution of m-(5-hydroxypyrimidino)hippuric acid (3.74 g, 12.98 mmol) in dimethylacetamide (25 mL) was heated until all the material had dissolved. This was then cooled to 0° C. and isobutylchloroformate (1.68 mL) was added in one portion followed by N-methylmorpholine (1.45 mL). After 10 minutes, ethyl 3-(N-gly)-amino-3-(3,5-diiodo-2-hydroxyphenyl)propionate hydrochloride (6.0 g, 10.82 mmol) was added in one portion followed by N-methylmorpholine (1.45 mL). The reaction mixture was stirred for 18 hours at room temperature. The reaction mixture was concentrated, the residue dissolved in tetrahydrofuran/water (1:1, 20 mL), and was chromatographed (reverse phase, 95:5 water: acetonitrile over 60 minutes to 30:70 water:acetonitrile containing 0.1% TFA). The combined fractions were concentrated. The residue was dissolved in acetonitrile water and lithium hydroxide was added until basic. The solution was stirred for 2 hours. The reaction mixture was concentrated and was purified as above by hplc to afford the desired acid as the TFA salt. The TFA salt was converted to the corresponding hydrochloride salt by passing through an ion-exchange column followed by lyophilization. $^1$H NMR was consistent with the desired product.

The activity of the $\alpha_v\beta_3$ integrin antagonist compounds of the present invention was tested in the following assays.

Vitronectin Adhesion Assay Materials

Human vitronectin receptor ($\alpha_v\beta_3$) was purified from human placenta as previously described [Pytela et al., *Meth- ods in Enzymology* 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3):1415–1421 (1991)]. Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods

Solid Phase Receptor Assays

This assay was essentially the same as previously reported [Niiya et al., *Blood*, 70:475–483 (1987)]. The purified human vitronectin receptor ($\alpha_v\beta_3$) was diluted from stock solutions to 1.0 g/mL in tris-buffered saline containing 1.0 mM $Ca^{++}$, $Mg^{++}$, and $Mn^{++}$, pH 7.4 (TBS$^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL of 1% RIA grade BSA in TBS$^{+++}$ (TBS$^{+++}$/BSA) were added to block exposed plastic surfaces. Following a 2 hour incubation, the assay plates were washed with TBS$^{+++}$ using a 96 well plate washer. Logarithmic serial dilution of the test compound and controls were made starting at a stock concentration of 2 mM and using 2 nM biotinylated vitronectin in TBS$^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was $1.0\times10^{-4}$ M. The competition occurred for two hours after which all wells were washed with a plate washer as before. Affinity purified horseradish peroxidase labeled goat anti-biotin antibody was diluted 1:3000 in TBS$^{+++}$/BSA and 125 μL were added to each well. After 30 minutes, the plates were washed and incubated with OPD/$H_2O$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)-amino]-1-oxopentyl]amino]-1-oxoethyl]amino]-3-pyridinepropanic acid [U.S. Ser. No. 08/375,338, Example 1] which is a potent $\alpha_v\beta_3$ antagonist ($IC_{50}$ in the range 3–10 nM) was included on each plate as a positive control.

Purified IIb/IIIa Receptor Assay

Materials

Human fibrinogen receptor ($\alpha_v\beta_3$) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", Blood 70(1987):475–483. The purified human fibrinogen receptor ($\alpha_{IIb}\beta_3$) was diluted from stock solutions to 1.0 µg/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 µL/well (100 ng receptor/well). The plates were sealed and incubated overnight at 4° C. to allow the receptor to bind to the wells. All remaining steps were at room temperature. The assay plates were emptied and 200 µL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 µL aliquots to the assay plate was carried out with a CETUS Propette robot; the final concentration of the labeled ligand was 1 nM and the highest concentration of test compound was $1.0 \times 10^{-4}$ M. The competition occurred for two hours after which all wells were washed with a plate washer as before. Affinity purified horseradish peroxidase labeled goat anti-biotin antibody was diluted 1:3000 in $TBS^{+++}$/BSA and 125 µL were added to each well. After 30 minutes, the plates were washed and incubated with $ODD/H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and %CV were determined for duplicate concentrations. The mean $A_{450}$ values were normalized to the mean of four maximum-binding controls (no competitor added) (B-MAX). The normalized values were subjected to a four parameter curve fit algorithm, [Robard et al., Int. Atomic Energy Agency, Vienna, pp 469 (1977)], plotted on a semilog scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$)in the range 3–10 nM) was included on each plate as a positive control.

Tumor Growth Inhibition

Tumor cells for implantation were taken from cells either grown in tissue culture (Leydig, M21) or serially passaged as tumors in mice and prepared as tumor brei (LLC, PC-3) by methodology known in the art. Mice were injected subcutaneously in the proximal dorsal midline with $5 \times 10^6$ tumor cells and administration of test $\alpha_v\beta_3$ integrin antagonist compound was initiated the evening of the same day either prior to the chemotherapeutic agent, delayed and on the same day as the chemotherapeutic agent or delayed and following the chemotherapeutic agent. Tumor volumes were measured at intervals over the course of the experiments. Tumors were measured with a vernier caliper and volumes were determined using the formula for the volume of a cylinder: tumor volume=$width^2 \times length \times 0.52$. Blood was routinely drawn, for serum calcium determination and plasma drug concentration, 6 hours post-dosing on day 4 or 5 and again 12 hours post-dosing on the day of sacrifice. On the final day of the experiment, tumors were dissected free and weighed. Calcium concentrations of serum samples were determined calorimetrically using a clinical diagnostic kit. The data are expressed as the mean +/- SEM. Student's and Mann-Whitney tests were used to assess differences between means or medians using the InStat software package.

XII was administered continuously beginning on day 1 after implantation of the tumor cells, and the chemotherapeutic, cisplatin, was administered as a single intraperitoneal dose of 10 mg/kg on day 5. In this study, cisplatin alone significantly retarded the grown of the LLC tumor. XII (1 and 10 mg/kg, oral, BID) did not affect the growth of the primary tumor mass. However, the combination of XII together with cisplatin resulted in an additive effect and a significant tumor growth delay (time to develop a tumor>500 $mm^3$ was: vehicle=18.1 days; cisplatin=22.4 days; cisplatin+XII at 10 mg/kg=27.3 days). The final tumor volume was also significantly reduced with the combination of cisplatin and XII. Moreover, the combination of cisplatin and XII resulted in a 39% improvement in median survival time over vehicle controls and an enhancement over either agent alone (28 days for the vehicle group; 33 days for the cisplatin group; 33 days for the XII group at 10 mg/kg group; 38 days for the combination group.)

An additive benefit with chemotherapy was also observed in the M21 human melanoma model using cyclophosphamide as the chemotherapeutic agent. In this model, cyclophosphamide was administered (150 mg/kg;ip) on days 14, 16 and 18, and XII (10 mg/kg, BID, PO) was administered continuously after the chemotherapeutic beginning on day 21. Cyclophosphamide significantly inhibited the growth of M21 tumors. Moreover, the addition of XII to chemotherapy provided additional therapeutic efficacy producing a 44% reduction in final tumor volume.

Taken together, these results demonstrate that $\alpha_v\beta_3$ antagonists administered to tumor bearing mice can delay the growth of these tumors when administered as sole therapy. Moreover, a benefit is observed when the $\alpha_v\beta_3$ antagonist is administered in combination with cytotoxic chemotherapy.

What is claimed is:

1. A method of treating cancer sensitive to the combination by administering to a mammal in need thereof an enhanced therapeutically effective amount of a compound of the formula

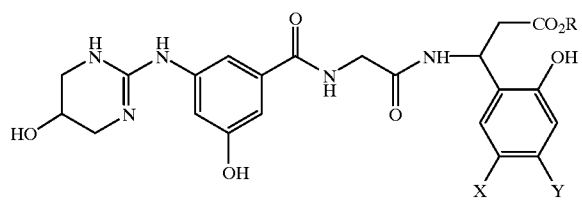

wherein X and Y are the same or different halo group; R is H or lower alkyl; and pharmaceutically acceptable salts thereof; together with an effective amount of a chemotherapeutic agent.

2. A method according to claim 1 wherein the chemotherapeutic agent is selected from the group consisting of cisplatin; cyclophosphamide; 5-fluorouracil, doxorubicin and taxol.

3. A method according to claim 1 wherein the compound is selected from the group consisting of:

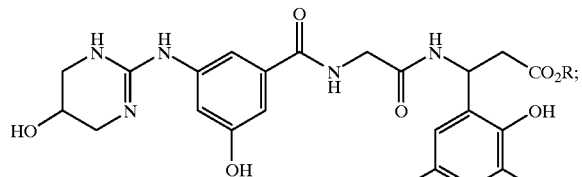

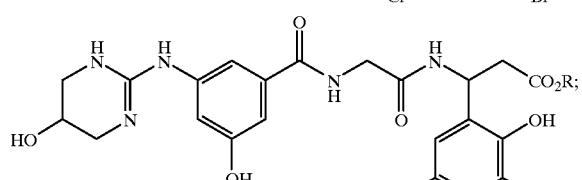

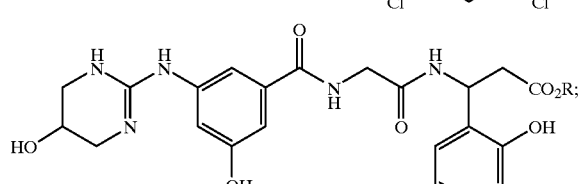

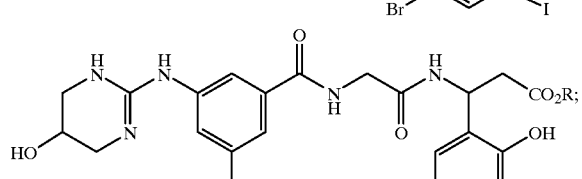

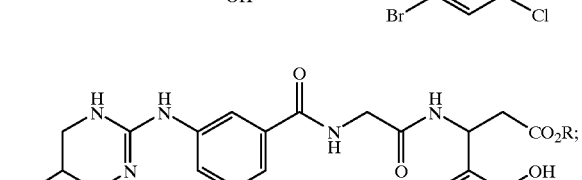

-continued

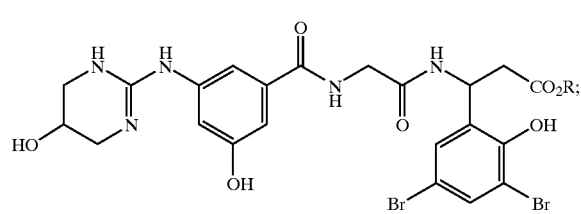

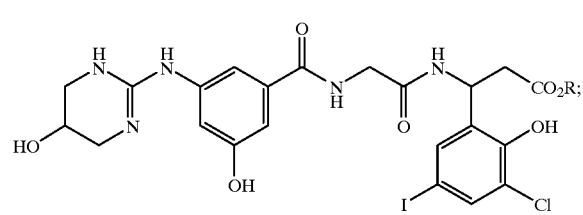

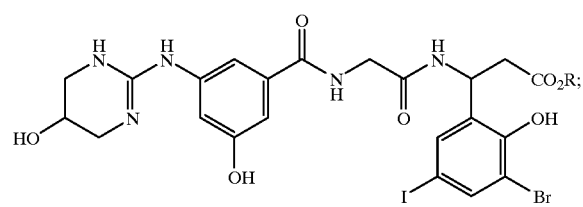

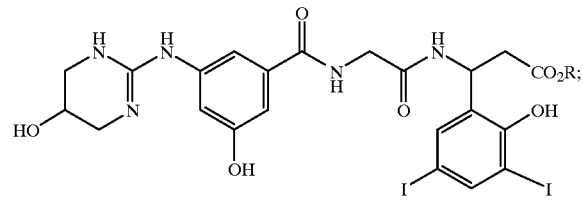

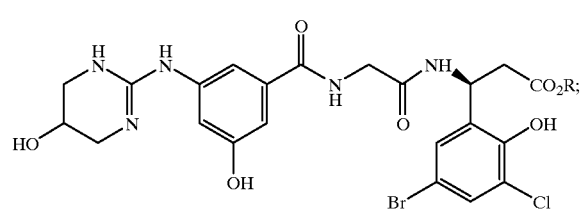

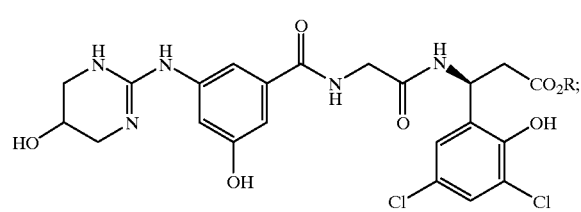

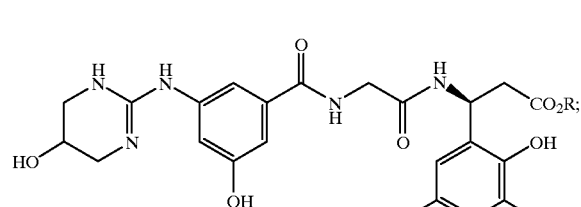

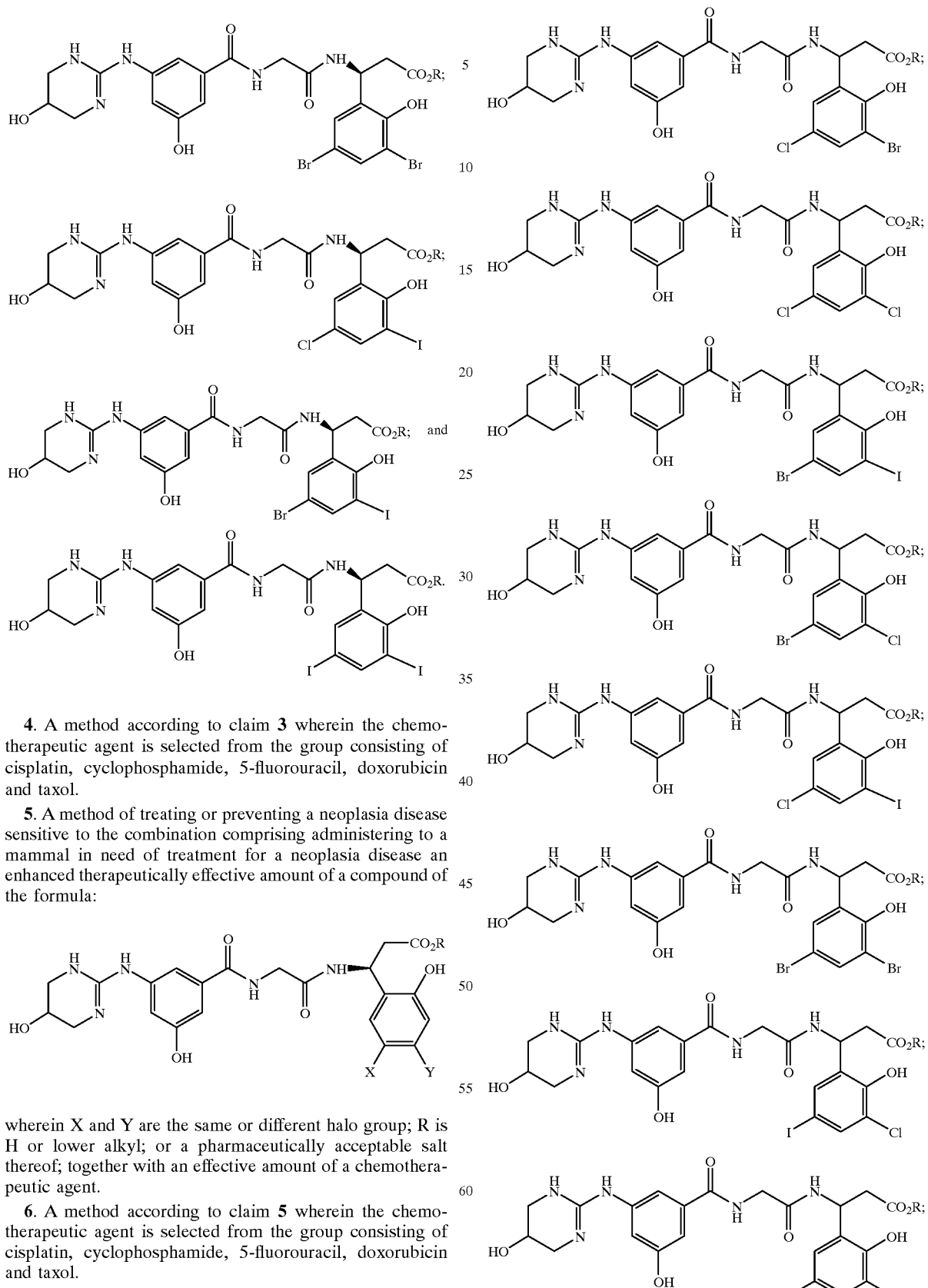

4. A method according to claim 3 wherein the chemotherapeutic agent is selected from the group consisting of cisplatin, cyclophosphamide, 5-fluorouracil, doxorubicin and taxol.

5. A method of treating or preventing a neoplasia disease sensitive to the combination comprising administering to a mammal in need of treatment for a neoplasia disease an enhanced therapeutically effective amount of a compound of the formula:

wherein X and Y are the same or different halo group; R is H or lower alkyl; or a pharmaceutically acceptable salt thereof; together with an effective amount of a chemotherapeutic agent.

6. A method according to claim 5 wherein the chemotherapeutic agent is selected from the group consisting of cisplatin, cyclophosphamide, 5-fluorouracil, doxorubicin and taxol.

7. A method according to claim 5 wherein the compound is selected from the group consisting of -continued

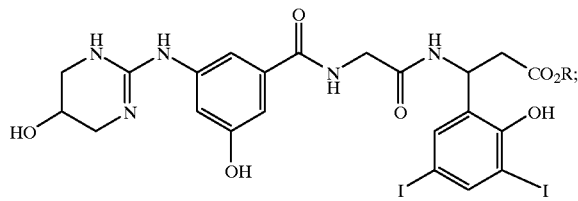

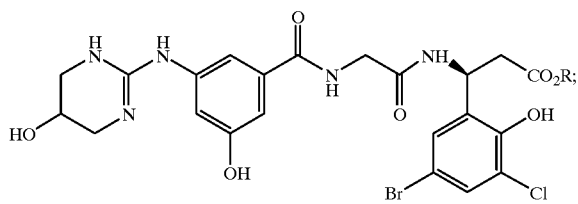

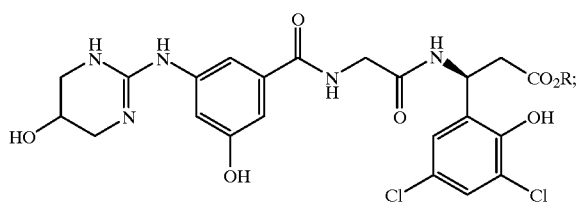

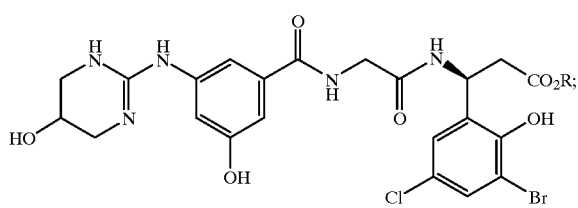

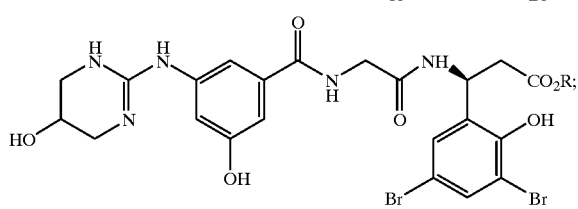

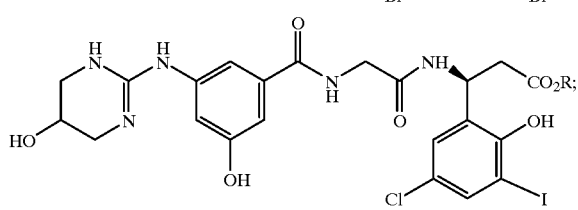

-continued

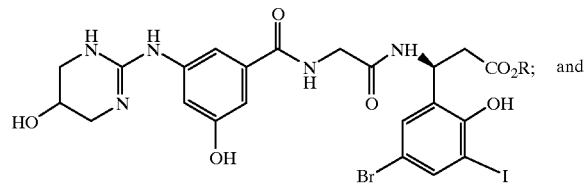

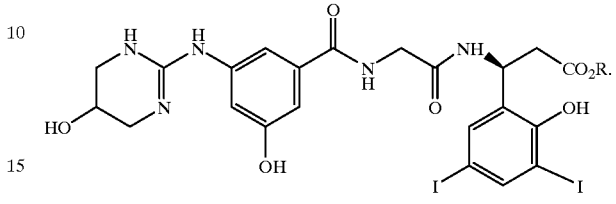

8. A method according to claim 7 wherein the chemotherapeutic agent is selected from the group consisting of cisplatin, cyclophosphamide, 5-fluorouracil, doxorubicin and taxol.

9. A method according to claim 5 wherein the neoplasia disease is tumor metastasis.

10. A method according to claim 5 wherein the neoplasia disease treated is solid tumor growth.

11. A method according to claim 5 wherein the condition treated is angiogenesis.

12. A method according to claim 5 wherein the neoplasia disease is humoral hypercalcemia of malignancy.

13. A pharmaceutical composition comprising an enhanced therapeutically effective amount of a compound according to claim 1, a chemotherapeutic agent and a pharmaceutically acceptable carrier.

* * * * *